US009549944B2

(12) United States Patent
Dubensky, Jr. et al.

(10) Patent No.: US 9,549,944 B2
(45) Date of Patent: Jan. 24, 2017

(54) COMPOSITIONS AND METHODS FOR INHIBITING "STIMULATOR OF INTERFERON GENE"—DEPENDENT SIGNALLING

(71) Applicant: ADURO BIOTECH, INC., Berkeley, CA (US)

(72) Inventors: Thomas W. Dubensky, Jr., Piedmont, CA (US); David B. Kanne, Corte Madera, CA (US)

(73) Assignee: ADURO BIOTECH, INC., Berkeley, CA (US)

( * ) Notice: Subject to any disclaimer, the term of this patent is extended or adjusted under 35 U.S.C. 154(b) by 47 days.

(21) Appl. No.: 14/280,668

(22) Filed: May 19, 2014

(65) Prior Publication Data
US 2014/0341976 A1    Nov. 20, 2014

Related U.S. Application Data

(63) Continuation of application No. PCT/US2014/038526, filed on May 18, 2014.

(60) Provisional application No. 61/825,009, filed on May 18, 2013.

(51) Int. Cl.
| A61K 31/70 | (2006.01) |
| A61K 39/00 | (2006.01) |
| A61K 39/36 | (2006.01) |
| A01N 43/04 | (2006.01) |
| C07H 21/00 | (2006.01) |
| A61K 31/7084 | (2006.01) |

(52) U.S. Cl.
CPC .................. A61K 31/7084 (2013.01)

(58) Field of Classification Search
CPC .................. A61K 31/7084
See application file for complete search history.

(56) References Cited

U.S. PATENT DOCUMENTS

| 5,547,941 | A | 8/1996 | Battistini et al. |
| 5,637,483 | A | 6/1997 | Dranoff et al. |
| 5,698,432 | A | 12/1997 | Oxford |
| 5,904,920 | A | 5/1999 | Dranoff et al. |
| 5,985,290 | A | 11/1999 | Jaffee et al. |
| 6,033,674 | A | 3/2000 | Jaffee et al. |
| 6,090,611 | A | 7/2000 | Covacci et al. |
| 6,277,368 | B1 | 8/2001 | Hiserodt et al. |
| 6,350,445 | B1 | 2/2002 | Jaffee et al. |
| 6,464,973 | B1 | 10/2002 | Levitsky et al. |
| 6,558,670 | B1 | 5/2003 | Friede et al. |
| 6,780,429 | B1 | 8/2004 | Matsuyama et al. |
| 7,569,555 | B2 | 8/2009 | Karaolis |
| 7,592,326 | B2 | 9/2009 | Karaolis |
| 7,709,458 | B2 | 5/2010 | Karaolis et al. |
| 8,012,469 | B2 | 9/2011 | Levitsky et al. |
| 8,283,328 | B2 * | 10/2012 | Krieg .......... A61K 31/70 514/44 R |
| 8,304,396 | B2 * | 11/2012 | Krieg .......... A61K 31/70 424/184.1 |
| 8,367,716 | B2 * | 2/2013 | Karaolis ............ 514/440 |
| 8,450,293 | B2 | 5/2013 | Jones et al. |
| 9,061,048 | B2 | 6/2015 | Portnoy et al. |
| 2001/0041682 | A1 | 11/2001 | Stutts et al. |
| 2002/0140414 | A1 | 10/2002 | Sohn et al. |
| 2002/0150588 | A1 | 10/2002 | Allison et al. |
| 2003/0138413 | A1 | 7/2003 | Vicari et al. |
| 2005/0281783 | A1 | 12/2005 | Kinch et al. |
| 2006/0040887 | A1 | 2/2006 | Karaolis |
| 2006/0286549 | A1 | 12/2006 | Sohn et al. |
| 2007/0059683 | A1 | 3/2007 | Barber et al. |
| 2007/0224210 | A1 | 9/2007 | Krieg et al. |
| 2007/0244059 | A1 | 10/2007 | Karaolis |
| 2007/0281897 | A1 | 12/2007 | Karaolis |
| 2008/0076778 | A1 | 3/2008 | Ossovskaya et al. |
| 2008/0286296 | A1 | 11/2008 | Ebensen et al. |
| 2010/0150946 | A1 | 6/2010 | Jooss et al. |
| 2010/0310602 | A1 | 12/2010 | Reed et al. |
| 2011/0081674 | A1 | 4/2011 | Han et al. |
| 2011/0262485 | A1 | 10/2011 | Barber |
| 2011/0287948 | A1 | 11/2011 | Suresh et al. |
| 2012/0041057 | A1 | 2/2012 | Jones et al. |
| 2012/0164107 | A1 | 6/2012 | Portnoy et al. |
| 2012/0178710 | A1 | 7/2012 | Jones et al. |
| 2014/0205653 | A1 | 7/2014 | Dubensky et al. |
| 2014/0329889 | A1 | 11/2014 | Vance et al. |

(Continued)

FOREIGN PATENT DOCUMENTS

| WO | 2005030186 A2 | 4/2005 |
| WO | 2005039535 A1 | 5/2005 |

(Continued)

OTHER PUBLICATIONS

Patel et al., Filing receipt plus Specification minus claims for U.S. Appl. No. 61/817,269, filed Apr. 29, 2013.*
Patel et al., Filing receipt minus Specification plus claims for U.S. Appl. No. 61/817,269, filed Apr. 29, 2013.*
O'Neill, Immunology. Sensing the dark side of DNA. Science. Feb. 15, 2013;339(6121):763-764.
Ora et al., Hydrolytic reactions of cyclic bis(3'-5')diadenylic acid (c-di-AMP). J Physical Organic Chem. 2013; 26(3):218-225.
Pardoll and Drake, Immunotherapy earns its spot in the ranks of cancer therapy. J Exp Med. Feb. 13, 2012;209(2):201-209.
Pardoll, The blockade of immune checkpoints in cancer immunotherapy. Nat Rev Cancer. Mar. 22, 2012;12(4):252-264.
Parvatiyar et al., DDX41 recognizes the bacterial secondary messengers cyclic di-GMP and cyclic di-AMP to activate a type I interferon immune response. Nat Immunol. Dec. 2012;13(12):1155-1161.
Prantner et al., 5,6-Dimethylxanthenone-4-acetic Acid (DMXAA) Activates Stimulator of Interferon Gene (STING)-dependent Innate Immune Pathways and Is Regulated by Mitochondrial Membrane Potential. J Biol Chem. Nov. 16, 2012;287(47):39776-39788.

(Continued)

Primary Examiner — Lawrence E Crane
(74) Attorney, Agent, or Firm — Michael A. Whittaker

(57) ABSTRACT

The present invention provides cyclic-di-nucleotide (CDN) compounds that inhibit signaling at a recently discovered cytoplasmic receptor known as STING (Stimulator of Interferon Genes). In particular, the CDNs of the present invention are provided in the form of a composition comprising one or more cyclic purine dinucleotides which inhibit STING-dependent TBK1 activation and the resulting production of type I interferon.

4 Claims, 11 Drawing Sheets

(56) References Cited

U.S. PATENT DOCUMENTS

| | | | |
|---|---|---|---|
| 2014/0341976 A1 | 11/2014 | Dubensky et al. | |
| 2015/0056224 A1 | 2/2015 | Dubensky et al. | |

FOREIGN PATENT DOCUMENTS

| | | | |
|---|---|---|---|
| WO | 2005087238 A2 | 9/2005 | |
| WO | 2005089777 A1 | 9/2005 | |
| WO | 2007054279 A2 | 5/2007 | |
| WO | 2010017248 A2 | 2/2010 | |
| WO | 2010067262 A1 | 6/2010 | |
| WO | 2010104883 A1 | 9/2010 | |
| WO | 2011003025 A1 | 1/2011 | |
| WO | 2011136828 A1 | 11/2011 | |
| WO | 2011139769 A2 | 11/2011 | |
| WO | 2012068360 A1 | 5/2012 | |
| WO | 2012088155 A1 | 6/2012 | |
| WO | 2012139209 A1 | 10/2012 | |
| WO | 2013086331 A1 | 6/2013 | |
| WO | 2013166000 A1 | 11/2013 | |
| WO | 2013185052 A1 | 12/2013 | |
| WO | 2014093936 A1 | 6/2014 | |
| WO | 2014099824 A1 | 6/2014 | |
| WO | 2014179760 A1 | 11/2014 | |
| WO | 2014189805 A1 | 11/2014 | |
| WO | 2014189806 A1 | 11/2014 | |
| WO | WO 2014/179335 A1 * | 11/2014 | |
| WO | 2015017652 A1 | 2/2015 | |
| WO | 2015061294 A2 | 4/2015 | |
| WO | 2015074145 A1 | 5/2015 | |
| WO | 2015077354 A1 | 5/2015 | |
| WO | 2015108595 A1 | 7/2015 | |
| WO | 2015185565 A1 | 12/2015 | |

OTHER PUBLICATIONS

Roembke et al., A cyclic dinucleotide containing 2-aminopurine is a general fluorescent sensor for c-di-GMP and 3',3'-cGAMP. Mol Biosyst. Jun. 2014;10(6):1568-1575.

Sawai et al., Preparation and Properties of Oligocytidylates with 2'-5' Internucleotide Linkage. Bull Chem Soc Jpn 1985;58(1)361-366.

Sawai et al., Synthesis of 2'-5' Linked Oligouridylates in Aqueous Medium Using the Pd2+ Ion. Chem Pharm Bull. 1981;29(8):2237-2245.

Shanahan et al., Identification of c-di-GMP Derivatives Resistant to an EAL Domain Phosphodiesterase. Biochemistry. Jan. 15, 2013;52(2):365-377.

Silverman, the Organic Chemistry of Drug Design and Drug Action, Published 1992 by Academic Press, pp. 352-397.

Stella, Prodrugs and Therapeutics. Expert Opinion on Therapeutic Patents 2004;14(3):277-280.

Sun and Bevan, Defective CD8 T Cell Memory Following Acute Infection Without CD4 T Cell Help. Science. Apr. 11, 2003;300(5617):339-342.

Tannock et al., Docetaxel plus Prednisone or Mitoxantrone plus Prednisone for Advanced Prostate Cancer. N Engl J Med. Oct. 7, 2004;351(15):1502-1512.

Testa et al., Prodrug Research: futile or fertile? Biochem Pharmacol. Dec. 1, 2004;68(11):2097-2106.

Tezuka et al., Synthesis of 2'-Modified Cyclic Bis(3'-5')diadenylic Acids (c-di-AMPs) and Their Promotion of Cell Division in a Freshwater Green Alga. Chem Lett. 41: 1723-25, 2012.

Tijono et al., Identification of human-selective analogues of the vascular-disrupting agent 5,6-dimethylxanthenone-4-acetic acid (DMXAA). Br J Cancer. Apr. 2, 2013;108(6):1306-1315.

Topalian et al., Cancer Immunotherapy Comes of Age. J Clin Oncol 2011.

Urata et al., Regio- and Diastereo-Selectivity of Montmorillonite-Catalyzed Oligomerization of Racemic Adenosine 5'-Phosphorimidazolide. Nucleosides Nucleotides Nucleic Acids. Apr. 2008;27(4):421-430.

Van Elsas et al., Elucidating the Autoimmune and Antitumor Effector Mechnaisms of a Treatment Based on Cytotoxic T Lymphocyte Antigen-4 Blockade in Combination with a B16 Melanoma Vaccine: Comparison of Prophylaxis and Therapy. J Exp Med. Aug. 20, 2001;194(4):481-489.

Waitz et al., Potent Induction of Tumor Immunity by Combining Tumor Cryoablation with Anti-CTLA-4 Therapy. Cancer Res. Jan. 15, 2012;72(2):430-439.

Woodward et al., Supporting Online Material for c-di-AMP Secreted by Intracellular Listeria monocytogenes Activates a Host Type I Interferon Response. May 27, 2010 on Science Express May 27, 2010;DOI:10.1126/science.1189801 (15 pages).

Wu et al., Cyclic GMP-AMP Is an Endogenous Second Messenger in Innate Immune Signaling by Cytosolic DNA. Science. Feb. 15, 2013;339(6121):826-830.

Yan and Aguilar, Synthesis of 3',5'-cyclic diguanylic acid (cdiGMP) using 1-(4-chlorophenyl)-4-ethoxypiperidin-4-yl as a protecting group for 2'-hydroxy functions of ribonucleosides. Nucleosides Nucleotides Nucleic Acids. 2007;26(2):189-204.

Zhang et al., Cyclic GMP-AMP Containing Mixed Phosphodiester Linkages Is an Endogenous High-Affinity Ligand for STING. Mol Cell. Jul. 25, 2013;51(2):226-235.

International Search Report and Written Opinion issued in PCT/US2013/044744 dated Nov. 7, 2013.

Extended European Search Report and Written Opinion issued in PCT/US2013/044744 (EP 13799826) dated Nov. 20, 2015.

Burdette et al., STING is a direct innate immune sensor of cyclic-di-GMP. Nature. Sep. 25, 2011;478(7370):515-518.

Search Report and Written Opinion issued by IPOS in Singapore patent application No. 11201407875U dated Sep. 15, 2015.

Non Final Office Action issued in U.S. Appl. No. 13/912,960 dated Jul. 15, 2015.

Non Final Office Action issued in U.S. Appl. No. 14/106,687 dated Nov. 20, 2015.

Non Final Office Action issued in U.S. Appl. No. 14/280,667 dated Nov. 19, 2015.

Non Final Office Action issued in U.S. Appl. No. 14/268,967 dated Nov. 9, 2015.

Abutaily et al., Cadherins, catenins and APC in pleural malignant mesothelioma. J Pathol. Nov. 2003;201(3):355-362.

Adler-Moore et al., Characterization of the murine Th2 response to immunization with liposomal M2e influenza vaccine. Vaccine. Jun. 15, 2011;29(27):4460-4468.

Aguilar et al., Endemic Venezuelan Equine Encephalitis in Northern Peru. Emerg Infect Dis. May 2004;10(5):880-888.

Ahmed et al., Assessing the Safety of Adjuvanted Vaccines. Sci Transl Med. Jul. 27, 2011;3(93):93rv2.

Ahn et al., All CVB Serotypes and Clinical Isolates Induce Irreversible Cytopathic Effects in Primary Cardiomyocytes. J Med Virol. Feb. 2005;75(2):290-294.

Altwein and Luboldt, Prognostic Factors for Carcinoma of the Prostate. Urol Int. 1999;63(1):62-71.

Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. May 2005;64(5):780-782.

Andersen and thor Straten, Survivin—a universal tumor antigen. Histol Histopathol. Apr. 2002;17(2):669-675.

Argani et al., Discovery of New Markers of Cancer through Serial Analysis of Gene Expression Prostate Stem Cell Antigen Is Overexpressed in Pancreatic Adenocarcinoma. Cancer Res. Jun. 1, 2001;61(11):4320-4324.

Arora et al., Identification of Differentially Expressed Genes in Oral Squamous Cell Carcinoma. Mol Carcinog. Feb. 2005;42(2):97-108.

Attoui et al., Comparative sequence analysis of American, European and Asian isolates of viruses in the genus *Coltivirus*. J Gen Virol. Oct. 1998;79 ( Pt 10):2481-2489.

Badovinac et al., Accelerated CD8+ T-cell memory and prime-boost response after dendritic-cell vaccination. Nat Med. Jul. 2005;11(7):748-756.

Bahjat et al., Cytosolic Entry Controls CD8+-T-Cell Potency during Bacterial Infection. Infect Immun. Nov. 2006;74(11):6387-6397.

(56) References Cited

OTHER PUBLICATIONS

Bahjat et al., Suppression of Cell-Mediated Immunity following Recognition of Phagosome-Confined Bacteria. PLoS Pathog. Sep. 2009;5(9):e1000568.

Bala et al., PLGA Nanoparticles in Drug Delivery: The State of the Art. Crit Rev Ther Drug Carrier Syst. 2004;21(5):387-422.

Baldwin et al., The Importance of Adjuvant Formulation in the Development of a Tuberculosis Vaccine. J Immunol. Mar. 1, 2012;188(5):2189-2197.

Barbanti-Brodano et al., Simian virus 40 infection in humans and association with human diseases: results and hypotheses. Virology. Jan. 5, 2004;318(1):1-9.

Barber, Cytoplasmic DNA innate immune pathways. Immunol Rev. Sep. 2011;243(1):99-108.

Barber, STING-dependent signaling. Nat Immunol. Sep. 20, 2011;12(10):929-930.

Barthold et al., Infectivity, disease patterns, and serologic profiles of reovirus serotypes 1, 2, and 3 in infant and weanling mice. Lab Anim Sci. Oct. 1993;43(5):425-430.

Battistini et al., Stereoselective Synthesis of Cyclic Dinucleotide Phosphorothioates. Tetrahedron, 1993;49(5):1115-1132.

Baurain et al., High Frequency of Autologous Anti-Melanoma CTL Directed Against an Antigen Generated by a Point Mutation in a New Helicase Gene. J Immunol. Jun. 1, 2000;164(11):6057-6066.

Bevanger et al., Competitive Enzyme Immunoassay for Antibodies to a 43,000-Molecular-Weight Francisella tularensis Outer Membrane Protein for the Diagnosis of Tularemia. J Clin Microbiol. May 1989;27(5):922-926.

Bhigjee et al., Sequence of the env gene of some KwaZulu-Natal, South African strains of HTLV type I. AIDS Res Hum Retroviruses. Sep. 1, 1999;15(13):1229-1233.

Biagini et al., Simultaneous measurement of specific serum IgG responses to five select agents. Anal Bioanal Chem. Jun. 2005;382(4):1027-1034.

Bondurant et al., Definition of an Immunogenic Region Within the Ovarian Tumor Antigen Stratum Corneum Chymotryptic Enzyme. Clin Cancer Res. May 1, 2005;11(9):3446-3454.

Brezniceanu et al., HMGB1 inhibits cell death in yeast and mammalian cells and is abundantly expressed in human breast carcinoma. FASEB J. Jul. 2003;17(10):1295-1297.

Brian and Baric, Coronavirus Genome Structure and Replication. Curr Top Microbiol Immunol. 2005;287:1-30.

Brinkmann et al., Novel Genes in the PAGE and GAGE Family of Tumor Antigens Found by Homology Walking in the dbEST Database. Cancer Res. Apr. 1, 1999;59(7):1445-1448.

Brockstedt et al., Killed but metabolically active microbes: a new vaccine paradigm for eliciting effector T-cell responses and protective immunity. Nat Med. Aug. 2005;11(8):853-860.

Bronte et al., Genetic Vaccination with "Self" Tyrosinase-related Protein 2 Causes Melanoma Eradication but not Vitiligo. Cancer Res. Jan. 15, 2000;60(2):253-258.

Brown et al., Complete Genomic Sequencing Shows that Polioviruses and Members of Human Enterovirus Species C Are Closely Related in the Noncapsid Coding Region. J Virol. Aug. 2003;77(16):8973-8984.

Brown, Variants of B19. Dev Biol (Basel). 2004;118:71-77.

Burdette and Vance, STING and the innate immune response to nucleic acids in the cytosol. Nat Immunol. Jan. 2013;14(1):19-26.

Burdette et al., STING is a direct innate immune sensor of cyclic di-GMP. Nature. Sep. 25, 2011;478(7370):515-518 doi:10.1038/nature10429.

Capdepont et al., New Insights in HTLV-I Phylogeny by Sequencing and Analyzing the Entire Envelope Gene. AIDS Res Hum Retroviruses. Jan. 2005;21(1):28-42.

Capurro et al., Glypican-3: A Novel Serum and Histochemical Marker for Hepatocellular Carcinoma. Gastroenterology. Jul. 2003;125(1):89-97.

Carbone et al., New developments about the association of SV40 with human mesothelioma. Oncogene. Aug. 11, 2003;22(33):5173-5180.

Chan et al., In Situ Hybridization Study of PSP94 (Prostatic Secretory Protein of 94 Amino Acids) Expression in Human Prostates. Prostate. Oct. 1, 1999;41(2):99-109.

Chang et al., A Phase I Trial of Tumor Lysate-Pulsed Dendritic Cells in the Treatment of Advanced Cancer. Clin Cancer Res. Apr. 2002;8(4):1021-1032.

Chen et al., Immunodominant CD41 responses identified in a patient vaccinated with full-length NY-ESO-1 formulated with ISCOMATRIX adjuvant. Proc Natl Acad Sci USA. Jun. 22, 2004;101(25):9363-9368.

Chern et al., Glycoprotein B Subtyping of Cytomegalovirus (CMV) in the Vitreous of Patients with AIDS and CMV Retinitis. J Infect Dis. Oct. 1998;178(4):1149-1153.

Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.

Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.

Clements et al., Adenomatous Polyposis Coli/β-Catenin Interaction and Downstream Targets: Altered Gene Expression in Gastrointestinal Tumors. Clin Colorectal Cancer. Aug. 2003;3(2):113-120.

Clifton et al., A chlamydial type III translocated protein is tyrosine-phosphorylated at the site of entry and associated with recruitment of actin. Proc Natl Acad Sci USA. Jul. 6, 2004;101(27):10166-10171.

Clinton et al., A Comparative Study of Four Serological Tumor Markers for the Detection of Breast Cancer. Biomed Sci Instrum. 2003;39:408-414.

Cobaleda et al., A primitive hematopoietic cell is the target for the leukemic transformation in human Philadelphia-positive acute lymphoblastic leukemia. Blood. Feb. 1, 2000;95(3):1007-1013.

Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.

Coffman et al., Vaccine adjuvants: putting innate immunity to work. Immunity. Oct. 29, 2010;33(4):492-503.

Gulmann et al., Adenomatous Polyposis Coli Gene, beta-Catenin, and E-Cadherin Expression in Proximal and Distal Gastric Cancers and Precursor Lesions. Appl Immunohistochem Mol Morphol. Sep. 2003;11(3):230-237.

Gupta et al., Refolding, purification, and crystallization of apical membrane antigen 1 from Plasmodium falciparum. Protein Expr Purif. May 2005;41(1):186-198.

Haddad et al., Novel antigen identification method for discovery of protective malaria antigens by rapid testing of DNA vaccines encoding exons from the parasite genome. Infect Immun. Mar. 2004;72(3):1594-1602.

Hakansson et al., Establishment and phenotypic characterization of human U937 cells with inducible P210 BCR/ABL expression reveals upregulation of CEACAM1 (CD66a). (2004) Leukemia 18:538-547.

Harris et al., The Biological and Therapeutic Importance of Gastrin Gene Expression in Pancreatic Adenocarcinomas. Cancer Res. Aug. 15, 2004;64(16):5624-5631.

Harty and Badovinac, Shaping and reshaping CD8+ T-cell memory. Nat Rev Immunol. Feb. 2008;8(2):107-19-119.

Hashido et al., Evaluation of an Enzyme-Linked Immunosorbent Assay Based on Binding Inhibition for Type-Specific Quantification of Poliovirus Neutralization-Relevant Antibodies. Microbiol Immunol. 1999;43(1):73-77.

Hassan et al., Mesothelin: A New Target for Immunotherapy. Clin Cancer Res. Jun. 15, 2004;10(12 Pt 1):3937-3942.

Havlasova et al., Mapping of immunoreactive antigens of Francisella tularensis live vaccine strain. Proteomics. Jul. 2002;2(7):857-867.

Havlasova et al., Proteomic analysis of anti-Francisella tularensis LVS antibody response in murine model of tularemia. Proteomics. May 2005;5(8):2090-2103.

(56) References Cited

OTHER PUBLICATIONS

Hayakawa, A facile synthesis of cyclic bis(30!50)diguanylic acid. Tetrahedron 2003;59:6465-6471.

He et al., Complexes of Poliovirus Serotypes with Their Common Cellular Receptor, CD155. J Virol. Apr. 2003;77(8):4827-4835.

Hirose et al., Incidence of Diffuse Large B-Cell Lymphoma of Germinal Center B-Cell Origin in Whole Diffuse Large B-Cell Lymphoma: Tissue Fluorescence In Situ Hybridization Using t(14;18) Compared with Immunohistochemistry. Int J Hematol. Jan. 2005;81(1):48-57.

Hoffman et al., Strategy for development of a pre-erythrocytic Plasmodium falciparum DNA vaccine for human use. Vaccine. Jun. 1997;15(8):842-845.

Hoke, History of U.S. Military Contributions to the Study of Viral Encephalitis. Mil Med. Apr. 2005;170(4 Suppl):92-105.

Hu et al., c-di-GMP as a vaccine adjuvant enhances protection against systemic methicillin-resistant *Staphylococcus aureus* (MRSA) infection. Vaccine. Jul. 30, 2009;27(35):4867-4873.

Hughes, Nanostructure-mediated drug delivery. Nanomedicine. Mar. 2005;1(1):22-30.

Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.

Hutchinson et al., Multiplex Analysis of Cytokines in the Blood of Cynomolgus Macaques Naturally Infected With Ebola Virus (Reston Serotype). J Med Virol. Nov. 2001;65(3):561-566.

Hyodo et al., Synthesis of cyclic bis(3'-5')diguanylic acid (c-di-GMP) analogs. Tetrahedron 2006;62:3089-3094.

Iacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 15, 2003;63(24):8614-8622.

Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.

Isherwood et al., Vaccination strategies for Francisella tularensis. Adv Drug Deilv Rev. Jun. 17, 2005;57(9):1403-1414.

Ishikawa and Barber, STING an Endoplasmic Reticulum Adaptor that Facilitates Innate Immune Signaling. Nature. Oct. 2, 2008;455(7213):674-678.

Ito et al., Prostate Carcinoma Detection and Increased Prostate-Specific Antigen Levels after 4 Years in Dutch and Japanese Males Who Had No Evidence of Disease at Initial Screening. Cancer. Jan. 15, 2005;103(2):242-250.

Iwasaki and Medzhitov, Regulation of adaptive immunity by the innate immune system. Science. Jan. 15, 2010;327(5963):291-295.

Jainkittivong and Langlais, Herpes B virus infection. Oral Surg Oral Med Oral Pathol Oral Radiol Endod. Apr. 1998;85(4):399-403.

Jamieson et al., Human Torovirus: A New Nosocomial Gastrointestinal Pathogen. J Infect Dis. Nov. 1998;178(5):1263-1269.

Jansen and Shaw, Human Papillomavirus Vaccines and Prevention of Cervical Cancer. Annu Rev Med. 2004;55:319-331.

Jin et al., Identification and characterization of a loss-of-function human MPYS variant. Genes Immun. Jun. 2011;12(4):263-269.

Jin et al., MPYS Is Required for IFN Response Factor 3 Activation and Type I IFN Production in the Response of Cultured Phagocytes to Bacterial Second Messengers Cyclic-di-AMP and Cyclic-di-GMP. J Immunol. Sep. 1, 2011;187(5):2595-2601.

Jung et al., Strategies Against Human Papillomavirus Infection and Cervical Cancer. J Microbiol. Dec. 2004;42(4):255-266.

Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.

Karaolis et al., Bacterial c-di-GMP Is an Immunostimulatory Molecule. J Immunol. Feb. 15, 2007;178(4):2171-2181.

Karaolis et al., Cyclic Di-GMP Stimulates Protective Innate Immunity in Bacterial Pneumonia. Infect Immun. Oct. 2007;75(10):4942-4950.

Kastenmuller et al., Protective T cell immunity in mice following protein-TLR7/8 agonist-conjugate immunization requires aggregation, type I IFN, and multiple DC subsets. J Clin Invest. May 2011;121(5):1782-1796.

Kaufman et al., Parvovirus B19 does not bind to membrane-associated globoside in vitro. Virology. Feb. 5, 2005;332(1):189-198.

Kawai and Akira, The role of pattern-recognition receptors in innate immunity: update on Toll-like receptors. Nat Immunol. May 2010;11(5):373-384.

Kedl et al., Comparative Sequence Analysis of the Reovirus S4 Genes from 13 Serotype 1 and Serotype 3 Field Isolates. J Virol. Jan. 1995;69(1):552-559.

Kim et al., Co-Crystal Structures of PKG Iβ (92-227) with cGMP and cAMP Reveal the Molecular Details of Cyclic-Nucleotide Binding. PLoS One. Apr. 19, 2011;6(4):e18413.

Kim et al., Comparison of HPV DNA vaccines employing intracellular targeting strategies. Gene Ther. Jun. 2004;11(12):1011-1018.

Krzych et al., T lymphocytes from volunteers immunized with irradiated Plasmodium falciparum sporozoites recognize liver and blood stage malaria antigens. J Immunol. Oct. 15, 1995;155(8):4072-4077.

Kubuschok et al., Expression of cancer testis antigens in pancreatic carcinoma cell lines, pancreatic adenocarcinoma and chronic pancreatitis. Int J Cancer. Apr. 20, 2004;109(4):568-575.

Kumamuru et al., T-cell receptor Vbeta gene usage by T cells reactive with the tumor-rejection antigen SART-1 in oral squamous cell carcinoma. Int J Cancer. Feb. 20, 2004;108(5):686-695.

Laheru and Jaffee, Immunotherapy for pancreatic cancer—science driving clinical progress. Nat Rev Cancer. Jun. 2005;5(6):459-467.

Lauvau et al., Priming of Memory But Not Effector CD8 T Cells by a Killed Bacterial Vaccine. Science. Nov. 23, 2001;294(5547):1735-1739.

Leber et al., Distinct TLR- and NLR-Mediated Transcriptional Responses to an Intracellular Pathogen. PLoS Pathog. Jan. 2008;4(1):e6.

Lee et al., A clinical grade cocktail of cytokines and PGE2 results in uniform maturation of human monocyte-derived dendritic cells: implications for immunotherapy. Vaccine. Dec. 19, 2002;20 Suppl 4:A8-A22.

Lee et al., Immunomic analysis of human sarcoma. Proc Natl Acad Sci U S A. Mar. 4, 2003;100(5):2651-2656.

Li et al., Advanced Glycation End Products Induce Tubular Epithelial-Myofibroblast Transition through the RAGE-ERK1/2 MAP Kinase Signaling Pathway. Am J Pathol. Apr. 2004;164(4):1389-1397.

Li et al., Expression Profile of Cancer-Testis Genes in 121 Human Colorectal Cancer Tissue and Adjacent Normal Tissue. Clin Cancer Res. Mar. 1, 2005;11(5):1809-1814.

Liang et al., Microvessel density, cyclo-oxygenase 2 expression, K-ras mutation and p53 overexpression in colonic cancer. Br J Surg. Mar. 2004;91(3):355-361.

Libanova et al., The member of the cyclic di-nucleotide family bis-(3', 5')-cyclic dimeric inosine monophosphate exerts potent activity as mucosal adjuvant Vaccine. Mar. 2, 2010;28(10):2249-2258.

Lim et al., Molecular and phenotypic spectrum of de novo Philadelphia positive acute leukemia. Int J Mol Med. Dec. 1999;4(6):665-667.

Lin et al., Melanoma-Associated Antigens in Esophageal Adenocarcinoma Identification of Novel MAGE-A10 Splice Variants. Clin Cancer Res. Sep. 1, 2004;10(17):5708-5716.

Lubong Sabado et al., In Vitro Priming Recapitulates In Vivo HIV-1 Specific T Cell Responses, Revealing Rapid Loss of Virus Reactive CD4+ T Cells in Acute HIV-1 Infection. PLoS One. 2009;4(1):e4256 (13 pages).

Lucas et al., MAGE-B5, MAGE-B6, MAGE-C2, and MAGE-C3: four new members of the MAGE family with tumor-specific expression. Int J Cancer. Jul. 1, 2000;87(1):55-60.

(56) References Cited

OTHER PUBLICATIONS

Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.
Madhun et al., Intranasal c-di-GMP-adjuvanted plant-derived H5 influenza vaccine induces multifunctional Th1 CD4+ cells and strong mucosal and systemic antibody responses in mice. Vaccine. Jul. 12, 2011;29(31):4973-4982.
Mandruzzato et al., A CASP-8 Mutation Recognized by Cytolytic T Lymphocytes on a Human Head and Neck Carcinoma. J Exp Med. Aug. 29, 1997;186(5):785-793.
Matsumoto et al., Expression of the SART-1 antigens in uterine cancers. Jpn J Cancer Res. Dec. 1998;89(12):1292-1295.
Matsushita et al., Preferentially Expressed Antigen of Melanoma (PRAME) in the Development of Diagnostic and Therapeutic Methods for Hematological Malignancies. Leuk Lymphoma. Mar. 2003;44(3):439-444.
Mayo et al., Mdm-2 Phosphorylation by DNA-dependent Protein Kinase Prevents Interaction with p53. Cancer Res. Nov. 15, 1997;57(22):5013-5016.
McCool et al., Roles of calreticulin and calnexin during mucin synthesis in LS180 and HT29/A1 human colonic adenocarcinoma cells. Biochem J. Aug. 1, 1999;341 ( Pt 3):593-600.
McCune et al., Active specific immunotherapy with tumor cells and Corynebacterium parvum: A phase I study. Cancer. May 1979;43(5):1619-1623.
McWhirter et al., A host type I interferon response is induced by cytosolic sensing of the bacterial second messenger cyclic-di-GMP. J Exp Med. Aug. 31, 2009;206(9):1899-1911.
Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.
Molijn et al., Molecular diagnosis of human papillomavirus (HPV) infections. J Clin Virol. Mar. 2005;32 Suppl 1: S43-51.
Moreau-Aubry et al., A Processed Pseudogene Codes for a New Antigen Recognized by a Cd8+ T Cell Clone on Melanoma. J Exp Med. May 1, 2000;191(9):1617-1624.
Morse et al., A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen. Clin Cancer Res. Jun. 1999;5(6):1331-1338.
Muderhwa et al., Oil-in-water liposomal emulsions: Characterization and potential use in vaccine delivery. J Pharm Sci. Dec. 1999;88(12):1332-1339.
Mukhopadhyay et al., A structural perspective of the flavivirus life cycle. Nat Rev Microbiol. Jan. 2005;3(1):13-22.
Mulders et al., Tumor antigens and markers in renal cell carcinoma. Urol Clin North Am. Aug. 2003;30(3):455-465.
Muller et al., MeCP2 and MBD2 expression in human neoplastic and non-neoplastic breast tissue and its association with oestrogen receptor status. Br J Cancer. Nov. 17, 2003;89(10):1934-1939.
Muminova et al., Characterization of human mesothelin transcripts in ovarian and pancreatic cancer. BMC Cancer. May 12, 2004;4:19.
Nair et al., Induction of cytotoxic T cell responses and tumor immunity against unrelated tumors using telomerase reverse transcriptase RNA transfected dendritic cells. Nat Med. Sep. 2000;6(9):1011-1017.
Nakatsura et al., Cellular and humoral immune responses to a human pancreatic cancer antigen, coactosin-like protein, originally defined by the SEREX method. Eur J Immunol. Mar. 2002;32(3):826-836.
Nakatsura et al., Glypican-3, overexpressed specifically in human hepatocellular carcinoma, is a novel tumor marker. Biochem Biophys Res Commun. Jun. 20, 2003;306(1):16-25.
Nakatsura et al., Identification of Glypican-3 as a Novel Tumor Marker for Melanoma. Clin Cancer Res. Oct. 1, 2004;10(19):6612-6621.

Nelson and Griswold, A computer program for calculating antibody affinity constants. Comput Methods Programs Biomed. Jul.-Aug. 1988;27(1):65-68.
Neumann et al., Identification of an HLA-DR-restricted peptide epitope with a promiscuous binding pattern derived from the cancer testis antigen HOM-MEL-40/SSX2. Int J Cancer. Nov. 20, 2004;112(4):661-668.
Nicoletto et al., BRCA-1 and BRCA-2 mutations as prognostic factors in clinical practice and genetic counselling. Cancer Treat Rev. Oct. 2001;27(5):295-304.
Oberste et al., Evidence for Frequent Recombination within Species Human Enterovirus B Based on Complete Genomic Sequences of All Thirty-Seven Serotypes. J Virol. Jan. 2004;78(2):855-867.
Oberthuer et al., The Tumor-Associated Antigen PRAME Is Universally Expressed in High-Stage Neuroblastoma and Associated with Poor Outcome. Clin Cancer Res. Jul. 1, 2004;10(13):4307-4313.
Ogunniyi et al., c-di-GMP is an Effective Immunomodulator and Vaccine Adjuvant Against Pneumococcal Infection. Vaccine. Aug. 26, 2008;26(36):4676-4685.
Oliveira-Ferreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.
O'Riordan et al., Innate recognition of bacteria by a macrophage cytosolic surveillance pathway. Proc Natl Acad Sci U S A. Oct. 15, 2002;99(21):13861-13866.
Orvell et al., Antigenic relationships between six genotypes of the small hydrophobic protein gene of mumps virus. J Gen Virol. Oct. 2002;83(Pt 10):2489-2496.
Otte et al., MAGE-A Gene Expression Pattern in Primary Breast Cancer. Cancer Res. Sep. 15, 2001;61(18):6682-6687.
Ouyang et al., Structural Analysis of the STING Adaptor Protein Reveals a Hydrophobic Dimer Interface and Mode of Cyclic di-GMP Binding. Immunity. Jun. 29, 2012;36(6):1073-1086.
Oyston and Quarry, Tularemia vaccine: past, present and future. Antonie Van Leeuwenhoek. May 2005;87(4):277-281.
Padilla et al., Imaging of the varicella zoster virion in the viral highways: Comparison with herpes simplex viruses 1 and 2, cytomegalovirus, pseudorabies virus, and human herpes viruses 6 and 7. J Med Virol. 2003;70 Suppl 1:S103-S110.
Patel et al., Development of a simple restriction fragment length polymorphism assay for subtyping of coxsackie B viruses. J Virol Methods. Sep. 15, 2004;120(2):167-172.
Peh et al., Frequent presence of subtype A virus in Epstein-Barr virus-associated malignancies. Pathology. Oct. 2002;34(5):446-450.
Pham et al., Exploiting cross-priming to generate protective CD8 T-cell immunity rapidly. Proc Natl Acad Sci U S A. Jul. 6, 2010;107(27):12198-12203.
Pisarev et al., Full-length dominant-negative survivin for cancer immunotherapy. Clin Cancer Res. Dec. 15, 2003;9(17):6523-6533.
Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. Nov. 2004;11(6):1008-1015.
Rappuoli et al., Vaccines for the twenty-first century society. Nat Rev Immunol. Nov. 4, 2011;11(12):865-872.
Reed et al., New horizons in adjuvants for vaccine development. Trends Immunol. Jan. 2009;30(1):23-32.
Renkvist et al., A listing of human tumor antigens recognized by T cells. Cancer Immunol Immunother. Mar. 2001;50(1):3-15.
Zimmerman et al., Expression of annexin II in conventional renal cell carcinoma is correlated with Fuhrman grade and clinical outcome. Virchows Arch. Oct. 2004;445(4):368-374.
Ziyaeyan et al., The Seroprevalence of Parvovirus BI9 Infection among To-Be-Married Girls, Pregnant Women, and Their Neonates in Shi raz, Iran. Jpn J Infect Dis. Apr. 2005;58(2):95-97.
International Search Report and Written Opinion issued in PCT/US2014/038525 dated Sep. 9, 2014.
International Search Report and Written Opinion issued in PCT/US2014/038526 dated Sep. 19, 2014.

(56) References Cited

OTHER PUBLICATIONS

International Search Report and Written Opinion issued in PCT/US2013/075189 dated Mar. 11, 2014.
Shu et al., Structure of STING bound to cyclic di-GMP reveals the mechanism of cyclic dinucleotide recognition by the immune system. Nat Struct Mol Biol. Jun. 24, 2012;19(7):722-724.
Tanaka and Chen, STING Specifies IRF3 phosphorylation by TBK1 in the Cytosolic DNA Signaling Pathway. Sci Signal. Mar. 6, 2012;5(214):ra20 (19 pages).
Coler et al. Development and Characterization of Synthetic Glucopyranosyl Lipid Adjuvant System as a Vaccine Adjuvant. PLoS One. Jan. 26, 2011;6(1):e16333.
Coughlin et al., Orally Bioavailable Anti-HBV Dinucleotide Acyloxyalkyl Prodrugs. Bioorg Med Chem Lett. Mar. 1, 2010;20(5):1783-1786.
Creighton et al., Mechanisms and catalysts of disulfide bond formation in proteins. Trends Biotechnol. Jan. 1995;13(1):18-23.
Crimmins et al., Listeria monocytogenes multidrug resistance transporters activate a cytosolic surveillance pathway of innate immunity. Proc Natl Acad Sci U S A. Jul. 22, 2008;105(29):10191-10196.
Dalerba et al., MAGE, BAGE and GAGE gene expression in human rhabdomyosarcomas. Int J Cancer. Jul. 1, 2001;93(1):85-90.
Damasus-Awatai and Freeman-Wang, Human papilloma virus and cervical screening. Curr Opin Obstet Gynecol. Dec. 2003;15(6):473-477.
Das et al., Evaluation of a Western Equine Encephalitis recombinant E1 protein for protective immunity and diagnostics. Antiviral Res. Nov. 2004;64(2):85-92.
Davies et al., Characterisation of a recombinant Fv fragment of anti-MUC1 antibody HMFG1. Cancer Lett. Jul. 29, 1994;82(2):179-184.
Davies et al., Coordinated Regulation of Accessory Genetic Elements Produces Cyclic Di-Nucleotides for V. cholerae Virulence. Cell. Apr. 13, 2012;149(2):358-370.
De Backer et al., Characterization of the GAGE Genes That Are Expressed in Various Human Cancers and in Normal Testis. Cancer Res. Jul. 1, 1999;59(13):3157-3165.
de Villiers et al., Classification of papillomaviruses. Virology. Jun. 20, 2004;324(1):17-24.
Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64(10):3653-3660.
Desmet and Ishii, Nucleic acid sensing at the interface between innate and adaptive immunity in vaccination. Nat Rev Immunol. Jun. 22, 2012;12(7):479-491.
Dessureault et al., A phase-I Trial Using a Universal GM-CSF-producing and CD40L-expressing Bystander Cell Line (GM.CD40L) in the Formulation of Autologous Tumor Cell-based Vaccines for Cancer Patients with Stage IV disease. Ann Surg Oncol. Feb. 2007;14(2):869-884.
Diner et al., The Innate Immune DNA Sensor cGAS Produces a Noncanonical Cyclic Dinucleotide that Activates Human STING. Cell Rep. May 30, 2013;3(5):1355-1361.
Disis and Cheever, HER-2/Neu Protein: A Target for Antigen-Specific Immunotherapy of Human Cancer. Adv Cancer Res. 1997;71:343-371.
Disis et al., Humoral Epitope-Spreading Following Immunization with a HER-2/neu Peptide Based Vaccine in Cancer Patients. J Clin Immunol. Sep. 2004;24(5):571-578.
Dosaka-Akita et al., Expression of N-Acetylglucosaminyltransferase V Is Associated with Prognosis and Histology in Non-Small Cell Lung Cancers. Clin Cancer Res. Mar. 1, 2004;10(5):1773-1779.
Dubensky and Reed, Adjuvants for cancer vaccines. Semin Immunol. Jun. 2010;22(3):155-161.
Duxbury et al., CEACAM6 as a novel target for indirect type 1 immunotoxin-based therapy in pancreatic adenocarcinoma. Biochem Biophys Res Commun. May 7, 2004;317(3):837-843.

Eager and Nemunaitis, GM-CSF Gene-Transduced Tumor Vaccines. Mol Ther. Jul. 2005;12(1):18-27.
Ebensen et al., Bis-(3',5')-cyclic dimeric adenosine monophosphate: Strong Th1/Th2/Th17 promoting mucosal adjuvant. Vaccine. Jul. 18, 2011;29(32):5210-5220.
Ebensen et al., The bacterial second messenger cyclic diGMP exhibits potent adjuvant properties. Vaccine. Feb. 9, 2007;25(8):1464-1469.
Ebensen et al., The Bacterial Second Messenger cdiGMP Exhibits Promising Activity as a Mucosal Adjuvant. Clin Vaccine Immunol. Aug. 2007;14(8):952-958.
Einstein et al., Comparison of the immunogenicity and safety of Cervarix and Gardasil human papillomavirus (HPV) cervical cancer vaccines in healthy women aged 18-45 years. Hum Vaccin. Oct. 2009;5(10):705-719.
Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbiol. May 1997;35(5):1122-1130.
Engels et al., Serologic Evidence for Exposure to Simian Virus 40 in North American Zoo Workers. J Infect Dis. Dec. 15, 2004;190(12):2065-2069.
Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.
Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.
Estrada-Franco et al., Venezuelan Equine Encephalitis Virus, Southern Mexico. Emerg Infect Dis. Dec. 2004;10(12):2113-2121.
Fang et al., Expression of Dnmt1, demethylase, MeCP2 and methylation of tumor-related genes in human gastric cancer. World J Gastroenterol. Dec. 1, 2004;10(23):3394-3398.
Faure et al., Inducible Hsp70 as Target of Anticancer Immunotherapy: Identification of HLA-A*0201-Restricted Epitopes. Int J Cancer. Mar. 1, 2004;108(6):863-870.
Fleishhauer et al., The DAM Gene Family Encodes a New Group of Tumor-specific Antigens Recognized by Human Leukocyte Antigen Al-restricted Cytotoxic T Lymphocytes. Cancer Res. Jul. 15, 1998;58(14):2969-2972.
Fong et al., Altered peptide ligand vaccination with Flt3 ligand expanded dendritic cells for tumor immunotherapy. Proc Natl Acad Sci U S A. Jul. 17, 2001;98(15):8809-8814.
Fuessel et al., Multiple tumor marker analyses (PSA, hK2, PSCA, trp-p8) in primary prostate cancers using quantitative RT-PCR. Int J Oncol. Jul. 2003;23(1):221-228.
Fujii et al., The VesiVax system: a method for rapid vaccine development. Front Biosci. Jan. 1, 2008;13:1968-1980.
Gaffney et al., One-Flask Syntheses of c-di-GMP and the [Rp,Rp] and [Rp,Sp] Thiophosphate Analogues. Org Lett. Jul. 16, 2010;12(14):3269-3271.
Gambus et al., Epitope mapping of a mouse monoclonal anti-MUC2 antibody suggests the existence of an immunodominant region in the COOH terminus of the MUC2 tandem-repeat sequence. Int J Cancer. Jan. 3, 1995;60(1):146-148.
Gao et al., Cyclic [G(20,50)pA(30,50)p] Is the Metazoan Second Messenger Produced by DNA-Activated Cyclic GMP-AMP Synthase. Cell. May 23, 2013;153(5):1094-1107.
Gao et al., Structure-Function Analysis of STING Activation by c[G(2',5')pA(3',5')p] and Targeting by Antiviral DMXAA. Cell. Aug. 15, 2013;154(4):748-762.
Geisbert and Jahrling, Differentiation of filoviruses by electron microscopy. Virus Res. Dec. 1995;39(2-3):129-150.
Ghazizadeh et al., Role of cdk4, p16INK4, and Rb Expression in the Prognosis of Bronchioloalveolar Carcinomas. Respiration. Jan.-Feb. 2005;72(1):68-73.
Gilliam et al., A phase II study of G17DT in gastric carcinoma. Eur J Surg Oncol. Jun. 2004;30(5):536-543.
Gonzalez et al., A comparative sequence analysis to revise the current taxonomy of the family Coronaviridae. Arch Virol. Nov. 2003;148(11):2207-2235.

(56) References Cited

OTHER PUBLICATIONS

Good et al., Development and regulation of cell-mediated immune responses to the blood stages of malaria: implications for vaccine research. Annu Rev Immunol. 2005;23:69-99.

Good et al., The immunological challenge to developing a vaccine to the blood stages of malaria parasites. Immunol Rev. Oct. 2004;201:254-267.

Grajkowski et al., Convenient Synthesis of a Propargylated Cyclic (3'-5') Diguanylic Acid and its "Click" Conjugation to a Biotinylated Azide. Bioconjug Chem. Nov. 17, 2010;21(11):2147-2152.

Grimm et al., Mouse alpha-fetoprotein-specific DNA-based immunotherapy of hepatocellular carcinoma leads to tumor regression in mice. Gastroenterology. Oct. 2000;119(4):1104-1112.

Groh et al., Efficient cross-priming of tumor antigen-specific T cells by dendritic cells sensitized with diverse anti-MICA opsonized tumor cells. Proc Natl Acad Sci USA. May 3, 2005;102(18):6461-6466.

Gueguen et al., An Antigen Recognized by Autologous CTLs on a Human Bladder Carcinoma. J Immunol. Jun. 15, 1998;160(12):6188-6194.

Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.

Rezig et al., Molecular Characterization of Coxsackievirus B5 Isolates. J Med Virol. Feb. 2004;72(2):268-274.

Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26(3):817-824.

Roden and Wu, Preventative and therapeutic vaccines for cervical cancer. Expert Rev Vaccines. Aug. 2003;2(4):495-516.

Roner et al., Identification of signals required for the insertion of heterologous genome segments into the reovirus genome. Proc Natl Acad Sci U S A. Dec. 19, 1995;92(26):12362-12366.

Ross et al., The Cyclic Diguanylic Acid Regulatory System of Cellulose Synthesis in Acetobacter xylinum. Chemical synthesis and biological activity of cyclic nucleotide dimer, trimer, and phosphothioate derivatives. J Biol Chem. Nov. 5, 1990;265(31):18933-18943.

Salazar-Onfray et al., Synthetic peptides derived from the melanocyte-stimulating hormone receptor MC1R can stimulate HLA-A2-restricted cytotoxic T lymphocytes that recognize naturally processed peptides on human melanoma cells. Cancer Res. Oct. 1, 1997;57(19):4348-4355.

Santin et al., The serine protease stratum corneum chymotryptic enzyme (kallikrein 7) is highly overexpressed in squamous cervical cancer cells. Gynecol Oncol. Aug. 2004;94(2):283-288.

Sarcevic et al., Expression of Cancer/Testis Tumor Associated Antigens in Cervical Squamous Cell Carcinoma. Oncology. 2003;64(4):443-449.

Sarobe et al., Carcinoembryonic Antigen as a Target to Induce Anti-Tumor Immune Responses. Curr Cancer Drug Targets. Aug. 2004;4(5):443-454.

Sasaki et al., SAGE mRNA expression in advanced-stage lung cancers. Eur J Surg Oncol. Dec. 2003;29(10):900-903.

Sasatomi et al., Expression of tumor rejection antigens in colorectal carcinomas. Cancer. Mar. 15, 2002;94(6):1636-1641.

Sauer et al., The N-Ethyl-N-Nitrosourea-Induced Goldenticket Mouse Mutant Reveals an Essential Function of Sting in the In Vivo Interferon Response to Listeria monocytogenes and Cyclic Dinucleotides. Infect Immun. Feb. 2011;79(2):688-694.

Scanlan et al., Antigens recognized by autologous antibody in patients with renal-cell carcinoma. Int J Cancer. Nov. 12, 1999;83(4):456-464.

Scanlan et al., Cancer-related serological recognition of human colon cancer: identification of potential diagnostic and immunotherapeutic targets. Cancer Res. Jul. 15, 2002;62(14):4041-4047.

Scanlan et al., Expression of cancer-testis antigens in lung cancer: definition of bromodomain testis-specific gene (BRDT) as a new CT gene, CT9. Cancer Lett. Mar. 31, 2000;150(2):155-164.

Scanlan et al., Humoral immunity to human breast cancer: antigen definition and quantitative analysis of mRNA expression. Cancer Immun. Mar. 30, 2001;1:4.

Scanlan et al., The cancer/testis genes: review, standardization, and commentary. Cancer Immun. Jan. 23, 2004;4:1.

Scarcella et al., Expression of MAGE and GAGE in high-grade brain tumors: a potential target for specific immunotherapy and diagnostic markers. Clin Cancer Res. Feb. 1999;5(2):335-341.

Schmidt et al., Memory CD8 T cell responses exceeding a large but definable threshold provide long-term immunity to malaria. Proc Natl Acad Sci U S A. Sep. 16, 2008;105(37):14017-14022.

Schmittgen et al., Expression of prostate specific membrane antigen and three alternatively spliced variants of PSMA in prostate cancer patients. Int J Cancer. Nov. 1, 2003;107(2):323-329.

Schwartz et al., Hyperinduction of Host Beta Interferon by a Listeria monocytogenes Strain Naturally Overexpressing the Multidrug Efflux Pump MdrT. Infect Immun. Apr. 2012;80(4):1537-1545.

Schwartz et al., Novel targeted and immunotherapeutic strategies in chronic myeloid leukemia. Semin Hematol. Jan. 2003;40(1):87-96.

Seder et al., T-cell quality in memory and protection: implications for vaccine design. Nat Rev Immunol. Apr. 2008;8(4):247-258.

Sepehr et al., Distinct pattern of TP53 mutations in squamous cell carcinoma of the esophagus in Iran. Oncogene. Nov. 1, 2001;20(50):7368-7374.

Shanahan et al., Differential analog binding by two classes of c-di-GMP riboswitches. J Am Chem Soc. Oct. 5, 2011;133(39):15578-15592.

Shigemasa et al., Expression of the protease inhibitor antileukoprotease and the serine protease stratum corneum chymotryptic enzyme (SCCE) is coordinated in ovarian tumors. Int J Gynecol Cancer. Nov.-Dec. 2001;11(6):454-461.

Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.

Shirasawa et al., Receptor for advanced glycation end-products is a marker of type I lung alveolar cells. Genes Cells. Feb. 2004;9(2):165-174.

Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64(11):3757-3760.

Shu et al., Structure of STING bound to c-di-GMP Reveals the Mechanism of Cyclic Dinucleotide Recognition by the Immune System. Nat Struct Mol Biol. Jun. 24, 2012;19(7):722-724.

Siegel et al., Induction of antitumour immunity using survivin peptide-pulsed dendritic cells in a murine lymphoma model. Br J Haematol. Sep. 2003;122(6):911-914.

Simon et al., Cervical response to vaccination against HPV16 E7 in case of severe dysplasia. Eur J Obstet Gynecol Reprod Biol. Aug. 15, 2003;109(2):219-223.

Singh et al., Avian influenza viral nucleocapsid and hemagglutinin proteins induce chicken CD8+ memory T lymphocytes. Virology 2010;399:231-238.

Singh et al., Non-replicating adenovirus vectors expressing avian influenza virus hemagglutinin and nucleocapsid proteins induce chicken specific effector, memory and effector memory CD8(+) T lymphocytes. Virology. Sep. 15, 2010;405(1):62-69.

Sjolander et al., Serological divergence of Dobrava and Saaremaa hantaviruses: evidence for two distinct serotypes. Epidemiol Infect. Feb. 2002;128(1):99-103.

Skoberne et al., KBMA Listeria monocytogenes is an effective vector for DC-mediated induction of antitumor immunity. J Clin Invest. Dec. 2008;118(12):3990-4001.

Slager et al., Identification of multiple HLA-DR-restricted epitopes of the tumor-associated antigen CAMEL by CD4+ Th1/Th2 lymphocytes. J Immunol. Apr. 15, 2004;172(8):5095-5102.

Slager et al., Induction of CAMEL/NY-ESO-ORF2-specific CD8+ T cells upon stimulation with dendritic cells infected with a modified Ad5 vector expressing a chimeric Ad5/35 fiber. Cancer Gene Ther. Mar. 2004;11(3):227-236.

(56) References Cited

OTHER PUBLICATIONS

Small et al., Immunotherapy of Hormone-Refractory Prostate Cancer With Antigen-Loaded Dendritic Cells. J Clin Oncol. Dec. 1, 2000;18(23):3894-3903.

Smith et al., Neutralization of HIV-1 Subtypes: Implications for Vaccine Formulations. J Med Virol. Nov. 1998;56(3):264-268.

Smits et al., Phylogenetic and Evolutionary Relationships among Torovirus Field Variants: Evidence for Multiple Intertypic Recombination Events. J Virol. Sep. 2003;77(17):9567-9577.

Sofia et al., Nucleoside, Nucleotide, and Non-Nucleoside Inhibitors of Hepatitis C Virus NS5B RNA—Dependent RNA—Polymerase. J Med Chem. Mar. 22, 2012;55(6):2481-2531.

Sofia, Nucleotide Prodrugs for HCV Therapy. Antivir Chem Chemother. Aug. 23, 2011;22(1):23-49.

Stams et al., Expression Levels ofTEL, AML1, and the Fusion ProductsTEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8):2974-2980.

Steffens et al., Immunohistochemical analysis of tumor antigen saturation following injection of monoclonal antibody G250. Anticancer Res. Mar.-Apr. 1999;19(2A):1197-1200.

Stirnadel et al., Assessment of different sources of variation in the antibody responses to specific malaria antigens in children in Papua New Guinea. Int J Epidemiol. Jun. 2000;29(3):579-586.

Stolier et al., Initial experience with surgical treatment planning in the newly diagnosed breast cancer patient at high risk for BRCA-1 or BRCA-2 mutation. Breast J. Nov.-Dec. 2004;10(6):475-480.

Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.

Sun et al., Cyclic GMP-AMP Synthase Is a Cytosolic DNA Sensor That Activates the Type I Interferon Pathway. Science. Feb. 15, 2013;339(6121):786-791.

Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.

Suzuki et al., Practical Synthesis of Cyclic Bis(3'-5')diadenylic Acid (c-di-AMP). Chem Lett. 2011;40(10):1113-1114.

Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8):1363-1370.

Tamayo et al., Roles of Cyclic Diguanylate in the Regulation of Bacterial Pathogenesis. Annu Rev Microbiol. 2007;61:131-148.

Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.

Tanaka and Chen, STING Specifies IRF3 Phosphorylation by TBK1 in the Cytosolic DNA Signaling Pathway. Sci Signal. Mar. 6, 2012;5(214):ra20.

Tanaka et al., Expression of Tumor-Rejection Antigens in Gynecologic Cancers. Jpn J Cancer Res. Nov. 2000;91(11):1177-1184.

Tannapfel et al., BRAF Gene Mutations Are Rare Events in Gastroenteropancreatic Neuroendocrine Tumors. Am J Clin Pathol. Feb. 2005;123(2):256-260I.

Tewari et al., Poly(I:C) is an effective adjuvant for antibody and multi-functional CD4+ T cell responses to Plasmodium falciparum circumsporozoite protein (CSP) and αDEC-CSP in Non Human Primates. Vaccine. Oct. 21, 2010;28(45):7256-7266.

Treurnicht et al., HHV-8 subtypes in South Africa: identification of a case suggesting a novel B variant. J Med Virol. Feb. 2002;66(2):235-240.

Trimble et al., Comparison of the CD8+ T cell responses and antitumor effects generated by DNA vaccine administered through gene gun, biojector, and syringe. Vaccine. Sep. 8, 2003;21(25-26):4036-4042.

Trincado et al., Human Cytomegalovirus Strains Associated With Congenital and Perinatal Infections. J Med Virol. Aug. 2000;61(4):481-487.

Tsang et al., Phenotypic Stability of a Cytotoxic T-Cell Line Directed Against an Immunodominant Epitope of Human Carcinoembryonic Antigen. Clin Cancer Res. Dec. 1997;3(12 Pt 1):2439-2449.

Tsao and Sober, Melanoma Treatment Update. Dermatol Clin. Apr. 2005;23(2):323-333.

Tsuruma et al., Phase I clinical study of anti-apoptosis protein, survivin-derived peptide vaccine therapy for patients with advanced or recurrent colorectal cancer. J Transl Med. Jun. 13, 2004;2(1):19 (11 pages).

Vallejo et al., Nucleotide Sequence and Restriction Fragment-Length Polymorphism Analysis of Human T-Cell Lymphotropic Virus Type II (HTLV-II) in Southern Europe: Evidence for the HTLV-IIa and HTLV-IIb Subtypes. J Acquir Immune Defic Syndr Hum Retrovirol. Dec. 1, 1996;13(4):384-391.

Van Den Eynde et al., A New Antigen Recognized by Cytolytic T Lymphocytes on a Human Kidney Tumor Results From Reverse Strand Transcription. J Exp Med. Dec. 20, 1999;190(12):1793-1800.

Van Erp et al., Application of a sol particle immunoassay to the determination of affinity constants of monoclonal antibodies. J Immunoassay. 1991;12(3):425-443.

Vance et al., Patterns of Pathogenesis: Discrimination of Pathogenic and Nonpathogenic Microbes by the Innate Immune System. Cell Host Microbe. Jul. 23, 2009;6(1):10-21.

Vandamme et al., African Origin of Human T-Lymphotropic Virus Type 2 (HTLV-2) Supported by a Potential New HTLV-2d Subtype in Congolese Bambuti Efe Pygmies. J Virol. May 1998;72(5):4327-4340.

Vilas Boas et al., Cytomegalovirus Glycoprotein B Genotypes and Central Nervous System Disease in AIDS Patients. J Med Virol. Nov. 2003;71(3):404-407.

Vilchez and Butel, Emergent Human Pathogen Simian Virus 40 and Its Role in Cancer. Clin Microbiol Rev. Jul. 2004;17(3):495-508.

Virok et al., Chlamydial Infection Induces Pathobiotype-Specific Protein Tyrosine Phosphorylation in Epithelial Cells. Infect Immun. Apr. 2005;73(4):1939-1946.

Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4):1687-1697.

Waltregny et al., Screening of histone deacetylases (HDAC) expression in human prostate cancer reveals distinct class I HDAC profiles between epithelial and stromal cells. Eur J Histochem. Jul.-Sep. 2004;48(3):273-290.

Wang et al., Alterations of APC, c-met, and p53 Genes in Tumor Tissue and Serum of Patients with Gastric Cancers. J Surg Res. Aug. 2004;120(2):242-248.

Wang et al., Cloning Genes Encoding MHC Class II—Restricted Antigens: Mutated CDC27 as a Tumor Antigen. Science. May 21, 1999;284(5418):1351-1354.

Wang et al., Identification of a Novel Major Histocompatibility Complex Class II—restricted Tumor Antigen Resulting from a Chromosomal Rearrangement Recognized by CD4+ T Cells. J Exp Med. May 17, 1999;189(10):1659-1668.

Ward et al., Binding activities of a repertoire of single immunoglobulin variable domains secreted from *Escherichia coli*. Nature. Oct. 12, 1989;341(6242):544-546.

Weaver et al., Genetic determinants of Venezuelan equine encephalitis emergence. Arch Virol Suppl. 2004; (18):43-64.

Weaver et al., Venezuelan Equine Encephalitis. Annu Rev Entomol. 2004;49:141-174.

Wells et al., Swine Influenza Virus Infections Transmission. From III Pigs to Humans at a Wisconsin Agricultural Fair and Subsequent Probable Person-to-Person Transmission. JAMA. Jan. 23-30, 1991;265(4):478-481.

Wentworth et al., An Influenza A (HINI) Virus, Closely Related to Swine Influenza Virus, Responsible for a Fatal Case of Human Influenza. J Virol. Apr. 1994;68(4):2051-2058.

(56) References Cited

OTHER PUBLICATIONS

Wille-Reece et al., HIV Gag protein conjugated to a Toll-like receptor 7/8 agonist improves the magnitude and quality of Th1 and CD8+ T cell responses in nonhuman primates. Proc Natl Acad Sci U S A. Oct. 18, 2005;102(42):15190-15194.
Wille-Reece et al., Immunization with HIV-1 Gag Protein Conjugated to a TLR7/8 Agonist Results in the Generation of HIV-1 Gag-Specific Th1 and CD8+ T Cell Responses. J Immunol. Jun. 15, 2005;174(12):7676-7683.
Wille-Reece et al., Toll-like receptor agonists influence the magnitude and quality of memory T cell responses after prime-boost immunization in nonhuman primates. J Exp Med. May 15, 2006;203(5):1249-1258.
Wilson et al., Simplified conjugation chemistry for coupling peptides to F(ab') fragments: autologous red cell agglutination assay for HIV-1 antibodies. J Immunol Methods. Oct. 14, 1994;175(2):267-273.
Witte et al., Innate Immune Pathways Triggered by Listeria monocytogenes and Their Role in the Induction of Cell-Mediated Immunity. Adv Immunol. 2012;113:135-156.
Woodward et al., c-di-AMP secreted by intracellular Listeria monocytogenes activates a host type I interferon response. Science. Jun. 25, 2010;328(5986):1703-1705.
Woycechowsky and Raines, Native Disulfide Bond Formation in Proteins. Curr Opin Chem Biol. Oct. 2000;4(5):533-539.
Yan et al., Synthesis and immunostimulatory properties of the phosphorothioate analogues of cdiGMP. Bioorg Med Chem Lett. Oct. 15, 2008;18(20):5631-5634.
Yarmush et al., Coupling of antibody-binding fragments to solid-phase supports: site-directed binding of F(ab')2 fragments. J Biochem Biophys Methods. Dec. 1992;25(4):285-297.
Yi et al., Single Nucleotide Polymorphisms of Human STING Can Affect Innate Immune Response to Cyclic Dinucleotides. PLoS One. Oct. 21, 2013;8(10):e77846.
Yin et al., Cyclic di-GMP Sensing via the Innate Immune Signaling Protein STING. Mol Mol Cell. Jun. 29, 2012;46(6):735-745.
Zaremba et al., Identification of an Enhancer Agonist Cytotoxic T Lymphocyte Peptide from Human Carcinoembryonic Antigen. Cancer Res. Oct. 15, 1997;57(20):4570-4577.
Zeier et al., New Ecological Aspects of Hantavirus Infection: A Change of a Paradigm and a Challenge of Prevention—A Review. Virus Genes. Mar. 2005;30(2):157-180.
Zhang et al., c-di-GMP Displays a Monovalent Metal Ion-Dependent Polymorphism. J Am Chem Soc. Dec. 29, 2004;126(51):16700-16701.
Zhao et al., Thiophosphate Analogs of c-di-GMP: Impact on Polymorphism. Nucleosides Nucleotides Nucleic Acids. May 2009;28(5):352-378.
Zhou et al., Endo-S-c-di-GMP Analogues-Polymorphism and Binding Studies with Class I Riboswitch. Molecules. Nov. 9, 2012;17(11):13376-13389.
Zhou et al., Potent suppression of c-di-GMP synthesis via I-site allosteric inhibition of diguanylate cyclases with 2'-F-c-di-GMP. Bioorg Med Chem. Jul. 15, 2013;21(14):4396-4404.
Ablasser et al., cGAS produces 2'-5'-linked cdn second messenger that activates STING. Nature. Jun. 20, 2013;498(7454):380-384.
Antonarakis and Drake, Combining immunological and androgen-directed approaches: an emerging concept in prostate cancer immunotherapy. Curr Opin Oncol. May 2012;24(3):258-265.
Ausmees et al., Genetic data indicate that proteins containing the GGDEF domain possess diguanylate cyclase activity. FEMS Microbiol Lett. Oct. 16, 2001;204(1):163-167.
Bahjat et al., Activation of Immature Hepatic NK Cells As Immunotherapy for Liver Metastatic Disease. J Immunol. Dec. 1, 2007;179(11):7376-7384.
Barker et al., STING-Dependent Recognition of Cyclic di-AMP Mediates Type I Interferon Responses during chlamydia trachomatis Infection. MBio. Apr. 30, 2013;4(3):e00018-e00013.
Blankenstein et al., The determinants of tumour immunogenicity. Nat Rev Cancer. Mar. 1, 2012;12(4):307-313.
Bowie et al., Innate Sensing of bacterial cdns: more than just STING. Nat Immunol. Dec. 2012;13(12):1137-1139.
Brahmer et al., Phase I Study of Single-Agent Anti-Programmed Death-1 (MDX-1106) in Refractory Solid Tumors: Safety, Clinical Activity, Pharmacodynamics, and Immunologic Correlates. J Clin Oncol. Jul. 1, 2010;28(19):3167-3175.
Brockstedt et al., Listeria-based cancer vaccines that segregate immunogenicity from toxicity. Proc Natl Acad Sci U S A. Sep. 21, 2004;101(38):13832-13837.
Burger's Medicinal Chemistry and Drug Discovery, Fifth Edition, published 1994 by Wiley-Interscience, edited by Manfred E. Wolff, pp. 975-977.
Chan et al., Structural basis of activity and allosteric control of diguanylate cyclase. Proc Natl Acad Sci U S A. Dec. 7, 2004;101(49):17084-17089.
Chen et al., The potential of 3',5'-cyclic diguanylic acid (c-di-GMP) as an effective vaccine adjuvant. Vaccine. Apr. 19, 2010;28(18):3080-3085.
Civril et al., Structural mechanism of cytosolic DNA sensing by cGAS. Nature. Jun. 20, 2013;498(7454):332-337.
Conlon et al., Mouse, but not Human STING, Binds and Signals in Response to the Vascular Disrupting Agent 5,6-Dimethylxanthenone-4-Acetic Acid. J Immunol. May 15, 2013;190(10):5216-5225.
Crittenden et al., Expression of Inflammatory Chemokines Combined with Local Tumor Destruction Enhances Tumor Regression and Long-term Immunity. Cancer Res. Sep. 1, 2003;63(17):5505-5512.
Curran and Allison, Tumor Vaccines Expressing Flt3 Ligand Synergize with CTLA-4 Blockade to Reject Preimplanted Tumors. Cancer Res. Oct. 1, 2009;69(19):7747-7755.
Dalby et al., Advanced transfection with Lipofectamine 2000 reagent: primary neurons, siRNA, and high-throughput applications. Methods. Jun. 2004;33(2):95-103.
de Grujil et al., Whole-cell cancer vaccination: from autologous to allogeneic tumor- and dendritic cell-based vaccines. Cancer Immunol Immunother. Oct. 2008;57(10):1569-1577.
Di Lorenzo et al., Immunotherapy for the treatment of prostate cancer. Nat Rev Clin Oncol. May 24, 2011;8(9):551-561.
Drake et al., Androgen ablation mitigates tolerance to a prostate/prostate cancer-restricted antigen. Cancer Cell. Mar. 2005;7(3):239-249.
Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-3543.
Driessens et al., Highly Successful Therapeutic Vaccinations Combining Factor Dendritic Cells and Tumo Cells Secreting Granulocyte Macrophage Colony-stimulating Factor. Cancer Res. Nov. 15, 2004;64(22):8435-8442.
Dubensky et al., Abstract 4573: A novel tumor vaccine with cyclic dinucleotides—can induce potent anti-tumor responses in vivo. Cancer Res. Apr. 15, 2013;73(8 Suppl):4573-4573.
Dubensky et al., Rationale, progress, and development of vaccines utilizing STING-activating cyclic dinucleotide adjuvants. Ther Adv Vaccines. Nov. 2013;1(4):131-143.
Ettmayer et al., Lessons Learned from Marketed and Investigational Prodrugs. J Med Chem. May 6, 2004;47(10):2393-2404.
Ertem and Ferris, Synthesis of RNA oligomers on heterogeneous templates. Nature. Jan. 18, 1996;379(6562)238-240.
Fasso et al., SPAS-1 (stimulator of prostatic adenocarcinoma-specific T cells)/SH3GLB2: A prostate tumor antigen identified by CTLA-4 blockade. Proc Natl Acad Sci U S A. Mar. 4, 2008;105(9):3509-3514.
Gao et al., GM-CSF-surface-modified B16.F10 melanoma cell vaccine. Vaccine. Jun. 19, 2006;24(25):5265-5268.
Goldberg et al., Role of PD-1 and its ligand, B7-H1, in early fate decisions of CD8 T cells. Blood. Jul. 1, 2007;110(1):186-192.
Gulley et al., Immunologic and Prognostic Factors Associated with Overall Survival Employing a Poxviral-based PSA Vaccine in Metastatic Castrate-resistant Prostate Cancer. Cancer Immunol Immunother. May 2010;59(5):663-674.

(56) References Cited

OTHER PUBLICATIONS

Hernandez et al., Novel Kidney Cancer Immunotherapy Based on the Granulocyte-Macrophage Colony-stimulating Factor and Carbonic Anhydrase IX Fusion Gene. Clin Cancer Res. May 2003;9(5):1906-1916.

Hodi et al., Improved Survival with Ipilimumab in Patients with Metastatic Melanoma. N Engl J Med. Aug. 19, 2010;363(8):711-723.

Huang et al., The structural basis for the sensing and binding of CDG by STING. Nat Struct Mol Biol. Jun. 24, 2012;19(7):728-730.

Hurwitz et al., The TRAMP Mouse as a Model for Prostate Cancer. Curr Protoc Immunol. Nov. 2001;Chapter 20:Unit 20.5.

Ishikawa and Barber, The STING pathway and regulation of innate immune signaling in response to DNA pathogens. Cell Mol Life Sci. Apr. 2011;68(7):1157-1165.

Jemal et al., Cancer statistics, 2010. CA Cancer J Clin. Sep.-Oct. 2010;60(5):277-300.

Kantoff et al., Sipuleucel-T Immunotherapy for Castration-Resistant Prostate Cancer. N Engl J Med. Jul. 29, 2010;363(5):411-422.

Kantoff et al., Overall Survival Analysis of a Phase II Randomized Controlled Trial of a Poxviral-Based PSA-Targeted Immunotherapy in Metastatic Castration-Resistant Prostate Cancer. J Clin Oncol. Mar. 1, 2010;28(7):1099-1105.

Krishnamachari et al., Nanoparticle Delivery Systems in Cancer Vaccines. Pharm Res 2011;28:215-236.

Lam et al, Adenovirus Detection by the cGAS/STING/TBK1 DNA Sensing Cascade. J Virol. Jan. 2014;88(2):974-981.

Le et al., A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction. Clin Cancer Res. Feb. 1, 2012;18(3):858-868.

Le et al., Cellular Vaccine Approaches. Cancer J. Jul.-Aug. 2010;16(4):304-10.

Li et al, Cyclic GMP-AMP Synthase Is Activated by Double-Stranded DNA-Induced Oligomerization. Immunity. Dec. 12, 2013;39(6):1019-1031.

Libanova, Cyclic di-nucleotides: new era for small molecules as adjuvants. Microb Biotechnol. Mar. 2012;5(2):168-176.

Luo et al, Selective binding of 2'-F-c-di-GMP to Ct-E88 and Cb-E43, new class I riboswitches from Clostridium tetani and Clostridium botulinum respectively. Mol Biosyst. Jun. 2013;9(6):1535-1539.

Lutz et al., A Lethally Irradiated Allogeneic Granulocyte-Macrophage Colony Stimulating Factor-Secreting Tumor Vaccine for Pancreatic Adenocarcinoma: A Phase II Trial of Safety, Efficacy, and Immune Activation. Ann Surg. Feb. 2011;253(2):328-335.

Mathew et al, Cytosolic delivery of antisense oligonucleotides by listeriolysin O-containing liposomes. Gene Ther. Jul. 2003;10(13):1105-1115.

Mellman et al., Cancer immunotherapy comes of age. Nature. Dec. 21, 2011;480(7378):480-489.

Miyabe et al., A new adjuvant delivery system 'cyclic di-GMP/YSK05 liposome' for cancer immunotherapy. J Control Release. Jun. 28, 2014;184:20-27 (author's version).

Olson et al., Liposomal gD Ectodomain (gD1-306) Vaccine Protects Against HSV2 Genital or Rectal Infection of Female and Male Mice. Vaccine. Dec. 11, 2009;28(2):548-560.

\* cited by examiner

X=O

COMPOSITIONS AND METHODS FOR INHIBITING "STIMULATOR OF INTERFERON GENE"—DEPENDENT SIGNALLING

This application is a continuation of International Application No. PCT/US2014/038526, filed May 18, 2014, which claims the benefit of Provisional Application No. 61/825,009 filed May 18, 2013, each of which is hereby incorporated by reference in its entirety.

BACKGROUND OF THE INVENTION

The following discussion of the background of the invention is merely provided to aid the reader in understanding the invention and is not admitted to describe or constitute prior art to the present invention.

The human immune system may generally be divided into two arms, referred to as "innate immunity" and "adaptive immunity." The innate arm of the immune system is predominantly responsible for an initial inflammatory response via a number of soluble factors, including the complement system and the chemokine/cytokine system; and a number of specialized cell types including mast cells, macrophages, dendritic cells (DCs), and natural killer cells. In contrast, the adaptive immune arm involves a delayed and a longer lasting antibody response together with CD8+ and CD4+ T cell responses that play a critical role in immunological memory against an antigen. A third arm of the immune system may be identified as involving γδ T cells and T cells with limited T cell receptor repertoires such as NKT cells and MAIT cells.

For an effective immune response to an antigen, antigen presenting cells (APCs) must process and display the antigen in a proper MHC context to a T cell, which then will result in either T cell stimulation of cytotoxic and helper T cells. Following antigen presentation successful interaction of co-stimulatory molecules on both APCs and T cells must occur or activation will be aborted. GM-CSF and IL-12 serve as effective pro-inflammatory molecules in many tumor models. For example, GM-CSF induces myeloid precursor cells to proliferate and differentiate into dendritic cells (DCs) although additional signals are necessary to activate their maturation to effective antigen-presenting cells necessary for activation of T cells. Barriers to effective immune therapies include tolerance to the targeted antigen that can limit induction of cytotoxic CD8 T cells of appropriate magnitude and function, poor trafficking of the generated T cells to sites of malignant cells, and poor persistence of the induced T cell response.

DCs that phagocytose tumor-cell debris process the material for major histocompatibility complex (MHC) presentation, upregulate expression of costimulatory molecules, and migrate to regional lymph nodes to stimulate tumor-specific lymphocytes. This pathway results in the proliferation and activation of CD4+ and CD8+ T cells that react to tumor-associated antigens. Indeed, such cells can be detected frequently in the blood, lymphoid tissues, and malignant lesions of patients.

New insights into the mechanisms underlying immune-evasion, together with combination treatment regimens that potentiate the potency of therapeutic vaccination—either directly or indirectly—through combination with immune checkpoint inhibitors or other therapies, have served as a basis for the development of vaccines that induce effective antitumor immunity. The CDNs cyclic-di-AMP (produced by *Listeria monocytogenes*) and its analog cyclic-di-GMP (produced by *Legionella pneumophila*) are recognized by the host cell as a PAMP (Pathogen Associated Molecular Pattern), which bind to the PRR (Pathogen Recognition Receptor) known as STING. STING is an adaptor protein in the cytoplasm of host mammalian cells which activates the TANK binding kinase (TBK1)-IRF3 signaling axis, resulting in the induction of IFN-β and other IRF-3 dependent gene products that strongly activate innate immunity. It is now recognized that STING is a component of the host cytosolic surveillance pathway, that senses infection with intracellular pathogens and in response induces the production of IFN-β, leading to the development of an adaptive protective pathogen-specific immune response consisting of both antigen-specific CD4 and CD8 T cells as well as pathogen-specific antibodies. Examples of cyclic purine dinucleotides are described in some detail in, e.g., U.S. Pat. Nos. 7,709,458 and 7,592,326; WO2007/054279; and Yan et al., Bioorg. Med. Chem Lett. 18: 5631 (2008), each of which is hereby incorporated by reference.

There remains a need for improved compositions and methods for immunologic strategies to treating diseases such as cancer that can be refractory to traditional therapeutic approaches.

SUMMARY OF THE INVENTION

It is an object of the present invention to provide combination therapies for the treatment of cancer.

In a first aspect, the present invention provides compositions comprising:
one or more cyclic purine dinucleotides ("CDNs") which that inhibit STimulator of INTerferon Gene ("STING")-dependent type I interferon production. As described hereinafter, a number of CDNs find use in the present invention. Preferred cyclic purine dinucleotides include, but are not limited to, one or more of c-di-AMP, c-di-GMP, c-di-IMP, c-AMP-GMP, c-AMP-IMP, c-GMP-IMP, and analogs thereof. This list is not meant to be limiting.

The general structure of a cyclic purine dinucleotide according to the present invention is as follows:

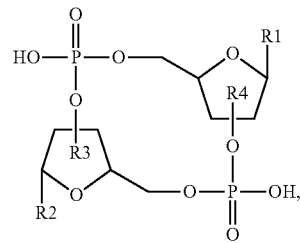

where each R1 and R2 is a purine, and the structure

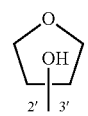

is intended to reflect that the phosphate linkage may be to either the 2' or 3' position on the ribose, and the other of the 2' or 3' position which is not participating in the cyclic linkage is an —OH. Thus, the present invention contemplates 2',5',2',5' CDNs, 2',5',3',5' CDNs, and 3',5',3',5' CDNs.

BY way of example, c-di-GMP having 3'-5' linkages refers to the molecule indicated above where each of R1 and R2 are guanine, and each phosphate linkage is 3'-to-5'.

For purposes of the present invention, this general structure is further modified to introduce substituents which confer the ability to inhibit STING-dependent signaling, and thereby inhibit STING-dependent type I interferon production. By way of example, the present invention provides compositions comprising the following compounds:

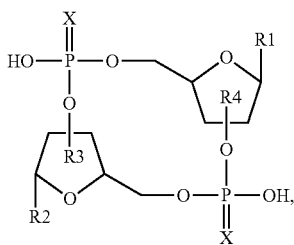

wherein each X is independently O or S, and R3 and R4 are each independently H or an optionally substituted straight chain alkyl of from 1 to 18 carbons and from 0 to 3 heteroatoms, an optionally substituted alkenyl of from 1-9 carbons, an optionally substituted alkynyl of from 1-9 carbons, or an optionally substituted aryl, wherein substitution(s), when present, may be independently selected from the group consisting of $C_{1-6}$ alkyl straight or branched chain, benzyl, halogen, trihalomethyl, $C_{1-6}$ alkoxy, —$NO_2$, —$NH_2$, —OH, =O, —COOR' where R' is H or lower alkyl, —$CH_2OH$, and —$CONH_2$, wherein R3 and R4 are not both H.

In preferred embodiments, one or both of R3 and R4 are independently an unsubstituted straight chain alkyl of from 1 to 18 carbons, an unsubstituted alkenyl of from 1-9 carbons, an unsubstituted alkynyl of from 1-9 carbons, or an unsubstituted aryl. In certain embodiments, one or both of R3 and R4 are allyl, propargyl, homoallyl, homopropargyl, methyl, ethyl, propyl, isopropyl, isobutyl, cyclopropylmethyl, or benzyl, either substituted or unsubstituted. In certain embodiments, one, but not both, or R3 and R4 provide a prodrug leaving group such as an aliphatic ester which is removed by cellular esterases.

In certain embodiments, each X is S. In preferred embodiments when each X is S, the compositions comprise one or more substantially pure Sp,Sp, Rp,Rp, Sp,Rp, or Rp,Sp stereoisomers.

In certain embodiments, each of R1 and R2 are independently selected from the group consisting of adenine, guanine, inosine, and xanthine or analogs thereof. Preferably, each of R1 and R2 are independently adenine or guanine.

As described hereinafter, a cyclic purine dinucleotide composition according to the present invention can inhibit STING-dependent type I interferon production at least 2-fold, and more preferably 5-fold or 10-fold, or more, as compared to c-di-GMP having 3'-5' linkages.

The compositions of the present invention may be administered to individuals in need thereof by a variety of parenteral and nonparenteral routes in formulations containing pharmaceutically acceptable carriers, adjuvants and vehicles. Preferred routes are parenteral, and include but, are not limited to, one or more of subcutaneous, intravenous, intramuscular, intraarterial, intradermal, intrathecal and epidural administrations. Particularly preferred is administration by subcutaneous administration. Preferred pharmaceutical compositions are formulated as aqueous, liposomal, or oil-in-water emulsions. Exemplary compositions are described hereinafter.

In related aspects, the present invention relates to methods of inhibiting or moderating an immune response in an individual, comprising administering a composition according to the present invention to an individual in need thereof. In other related aspects, the present invention relates to methods of inhibiting or moderating type I interferon production in an individual, comprising administering a composition according to the present invention to an individual in need thereof. Examples of autoimmune diseases which may be treated using the compositions of the present invention include, but are not limited to, alopecia areata, autoimmune hemolytic anemia, autoimmune hepatitis, dermatomyositis, diabetes (type 1), autoimmune juvenile idiopathic arthritis, glomerulonephritis, Graves' disease, Guillain-Barré syndrome, idiopathic thrombocytopenic purpura, lupus, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, some forms of thyroiditis, some forms of uveitis, vitiligo, and granulomatosis with polyangiitis (Wegener's).

In other embodiments, the methods described herein can comprise administering to the mammal an effective amount of the substantially pure CDNs of the present invention for the treatment of disorders in which shifting of Th1 to Th2 immunity confers clinical benefit. Cell-mediated immunity (CMI) is associated with TH1 CD4+ T lymphocytes producing cytokines IL-2, interferon (IFN)-γ and tumor necrosis factor (TNF)-α. In contrast, humoral immunity is associated with TH2 CD4+ T lymphocytes producing IL-4, IL-6 and IL-10 Immune deviation towards TH1 responses typically produces activation of cytotoxic T-cell lymphocytes (CTL), natural killer (NK) cells, macrophages and monocytes. Generally, Th1 responses are more effective against intracellular pathogens (viruses and bacteria that are inside host cells) and tumors, while Th2 responses are more effective against extracellular bacteria, parasites including helminths and toxins. Type I interferons (IFNs-I) are believed to mediate the lethal effects of endotoxemia and sepsis, and so the methods and compositions of the present invention can find use in the treatment of sepsis. In addition, the activation of innate immunity is expected to normalize the T-helper type 1 and 2 (Th1/Th2) immune system balance and to suppress the excessive reaction of Th2 type responses that cause immunoglobulin (Ig) E-dependent allergies and allergic asthma.

DETAILED DESCRIPTION OF THE INVENTION

Figure 1:
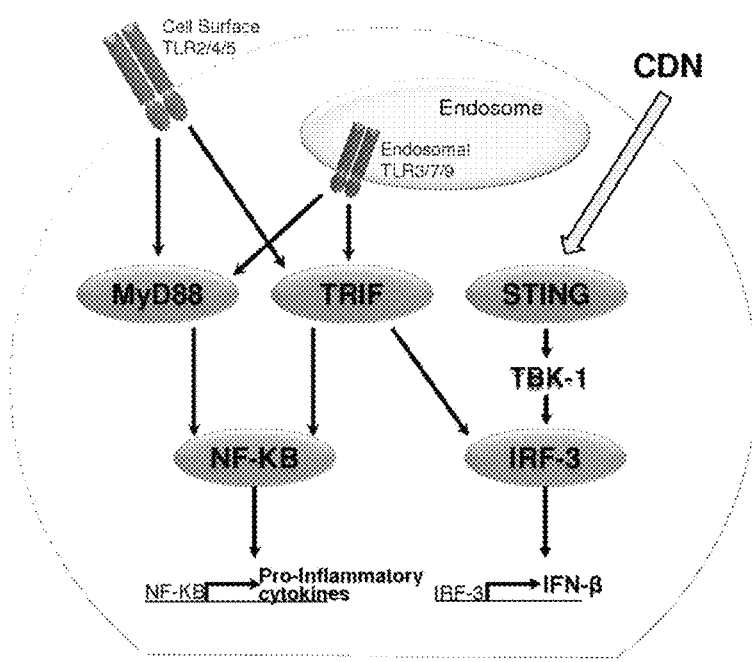
FIG. 1 depicts cyclic purine dinucleotide ("CDN")-mediated signaling. A CDN (e.g., c-di-AMP or c-di-GMP) induces production of IFN-β by binding to the cytosolic adaptor protein STING (Stimulator of Interferon Genes), and inducing signaling through the TBK-1/IRF-3 pathway, resulting in both autocrine and paracrine activation of DCs through binding to the IFN receptor and subsequent signaling.

The present invention relates to the use of novel cyclic-di-nucleotide (CDN) compounds that inhibit signaling at a recently discovered cytoplasmic receptor known as STING (Stimulator of Interferon Genes). In particular, the CDNs of the present invention are provided in the form of a composition comprising one or more cyclic purine dinucleotides which inhibit STING-dependent TBK1 activation and the resulting production of type I interferon.

The CDNs cyclic-di-AMP (produced by *Listeria monocytogenes*) and its analog cyclic-di-GMP (produced by *Legionella pneumophila*) are recognized by the host cell as a PAMP (Pathogen Associated Molecular Pattern), which bind to the PRR (Pathogen Recognition Receptor) known as STING. STING is an adaptor protein in the cytoplasm of host mammalian cells which activates the TANK binding kinase (TBK1)-IRF3 signaling axis, resulting in the induction of IFN-γ and other IRF-3 dependent gene products that strongly activate innate immunity. It is now recognized that STING is a component of the host cytosolic surveillance pathway, that senses infection with intracellular pathogens and in response induces the production of IFN, leading to the development of an adaptive protective pathogen-specific immune response consisting of both antigen-specific CD4 and CD8 T cells as well as pathogen-specific antibodies.

In the case of autoimmune diseases, inhibitors of this pathway can provide a novel therapeutic route which has not been previously exploited.

Definitions

"Administration" as it is used herein with regard to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell. By "administered together" it is not meant to be implied that two or more agents be administered as a single composition. Although administration as a single composition is contemplated by the present invention, such agents may be delivered to a single subject as separate administrations, which may be at the same or different time, and which may be by the same route or different routes of administration.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) can encompass GM-CSF, a mutein or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

By "substantially purified" with regard to CDNs of the invention is meant that a specified species accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the CDN activity present in a composition. The weights of water, buffers, salts, detergents, reductants, protease inhibitors, stabilizers (including an added protein such as albumin), and excipients are generally not used in the determination of purity.

"Specifically" or "selectively" binds, when referring to a ligand/receptor, nucleic acid/complementary nucleic acid, antibody/antigen, or other binding pair (e.g., a cytokine to a cytokine receptor) (each generally referred to herein as a "target biomolecule" or a "target") indicates a binding reaction which is related to the presence of the target in a heterogeneous population of proteins and other biologics. Specific binding can mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with a non-target molecule.

"Ligand" refers to a small molecule, nucleic acid, peptide, polypeptide, saccharide, polysaccharide, glycan, glycoprotein, glycolipid, or combinations thereof that binds to a target biomolecule. While such ligands may be agonists or antagonists of a receptor, a ligand also encompasses a binding agent that is not an agonist or antagonist, and has no agonist or antagonist properties. Specific binding of a ligand for its cognate target is often expressed in terms of an "Affinity." In preferred embodiments, the ligands of the present invention bind with affinities of between about $10^4$ $M^{-1}$ and about $10^8$ $M^{-1}$. Affinity is calculated as $K_a=k_{off}/k_{on}$ ($k_{off}$ is the dissociation rate constant, $K_{on}$ is the association rate constant and $K_d$ is the equilibrium constant).

Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988. In an alternative, affinity can be measured by isothermal titration calorimetry (ITC). In a typical ITC experiment, a solution of ligand is titrated into a solution of its cognate target. The heat released upon their interaction (ΔH) is monitored over time. As successive amounts of the ligand are titrated into the ITC cell, the quantity of heat absorbed or released is in direct proportion to the amount of binding. As the system reaches saturation, the heat signal diminishes until only heats of dilution are observed. A binding curve is then obtained from a plot of the heats from each injection against the ratio of ligand and binding partner in the cell. The binding curve is analyzed with the appropriate binding model to determine $K_B$, n and ΔH. Note that $K_B=1/K_d$.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a particular cancer which is being targeted by the compositions and methods of the present invention. Preferred cancers for treatment with the compositions described herein include, but are not limited to prostate cancer, renal carcinoma, melanoma, pancreatic cancer, cervical cancer, ovarian cancer, colon cancer, head & neck cancer, lung cancer and breast cancer.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: preventing a disease, improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: preventing a condition, improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Cyclic Purine Dinucleotides

Prokaryotic as well as eukaryotic cells use various small molecules for cell signaling and intra- and intercellular communication. Cyclic nucleotides like cGMP, cAMP, etc. are known to have regulatory and initiating activity in pro- and eukaryotic cells. Unlike eukaryotic cells, prokaryotic cells also use cyclic purine dinucleotides as regulatory molecules. In prokaryotes, the condensation of two GTP molecules is catalyst by the enzyme diguanylate cyclase (DGC) to give c-diGMP, which represents an important regulator in bacteria.

Recent work suggests that cyclic diGMP or analogs thereof can also stimulate or enhance immune or inflammatory response in a patient or can enhance the immune response to a vaccine by serving as an adjuvant in mammals.

Cytosolic detection of pathogen-derived DNA requires signaling through TANK binding kinase 1 (TBK1) and its downstream transcription factor, IFN-regulatory factor 3 (IRF3). A transmembrane protein called STING (stimulator of IFN genes; also known as MITA, ERIS, MPYS and TMEM173) functions as the signaling receptor for these cyclic purine dinucleotides, causing stimulation of the TBK1-IRF3 signalling axis and a STING-dependent type I interferon response. See, e.g., FIG. 1. Burdette et al., Nature 478: 515-18, 2011 demonstrated that STING binds directly to cyclic diguanylate monophosphate, but not to other unrelated nucleotides or nucleic acids.

Cyclic purine dinucleotides for use as precursors to derive the CDNs of the present invention are described in some detail in, e.g., Gao et al., Cell (2013) 153: doi: 10.1016/j.cell.2013.04.046; U.S. Pat. Nos. 7,709,458 and 7,592,326; WO2007/054279; and Yan et al., Bioorg. Med. Chem Lett. 18: 5631 (2008), each of which is hereby incorporated by reference. These CDNs may be modified using standard organic chemistry techniques in order to produce the CDNs of the present invention.

Preferred purines include, but are not limited to, adenine, guanine, inosine, hypoxanthine, xanthine, isoguanine, etc. The CDNs of the present invention are preferably phosphorothioate analogues, and most preferably substantially pure Sp,Sp, Rp,Rp, SpRp, or Rp,Sp stereoisomers thereof.

As denoted in the structures, each ribose comprises a 2' or 3' hydroxyl which may be substituted. As described hereinafter, the CDNs of the present invention can comprise a substitution at one or both of these 2' or 3' hydroxyls (which is not part of the cyclic linkage) which provide a blocking moiety that is not removed as a prodrug leaving group. Such substitutions include, but are not limited to, O-methyl, O-ethyl, O-propyl, O-isopropyl, O-benzyl, O-methoxyethyl, O-aminoethyl, O-propargyl, O-allyl, etc. This list is not meant to be limiting. The term "prodrug" as used herein refers to a modification of contemplated compounds, wherein the modified compound exhibits less pharmacological activity (as compared to the modified compound) and wherein the modified compound is converted within the body (e.g., in a target cell or target organ) back into the unmodified form through enzymatic or non-enzymatic reactions. In certain embodiments, the hydroxyl on one ribose comprises a prodrug leaving group. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011.

Preferred cyclic purine dinucleotides are phosphorothioate analogues, referred to herein as "thiophosphates". Phosphorothioates are a variant of normal nucleotides in which one of the nonbridging oxygens is replaced by a sulfur. The sulfurization of the internucleotide bond dramatically reduces the action of endo- and exonucleases, including 5' to 3' and 3' to 5' DNA POL 1 exonuclease, nucleases S1 and P1, RNases, serum nucleases and snake venom phosphodiesterase. In addition, the potential for crossing the lipid bilayer increases.

A phosphorothioate linkage in inherently chiral. The skilled artisan will recognize that the phosphates in this structure may each exist in R or S forms. Thus, Rp,Rp, Sp,Sp, Sp,Rp, and Rp,Sp forms are possible.

As noted above, cyclic purine dinucleotides of the present invention comprise 2'-O— and 3'-O— substituent forms of CDNs, and in particular CDN thiophosphates. Additional stability and bioavailability can be provided by the substitution of the 2'-OH of the ribose moiety. Substituent groups amenable herein include without limitation, halogen, hydroxyl, alkyl, alkenyl, alkynyl, acyl (—C(O)$R_{aa}$), carboxyl (—C(O)0-$R_{aa}$), aliphatic groups, alicyclic groups, alkoxy, substituted oxy (-0-$R_{aa}$), aryl, aralkyl, heterocyclic radical, heteroaryl, heteroarylalkyl, amino (—N($R_{bb}$)($R_{cc}$)), imino (=$NR_{bb}$), amido (—C(O)N($R_{bb}$)(Rc$_c$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)—N(Rbb)(Rcc)), thioureido (—N($R_{bb}$)C(S)N($R_{bb}$)($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)(Rc$_c$) or —N($R_{bb}$)C(=$NR_{bb}$)($R_{aa}$)), thiol (—S$R_{bb}$), sulfinyl (—S(O)$R_{bb}$), sulfonyl (—S(O)$_2R_b$) and sulfonamidyl (—S(O)$_2$N($R_{bb}$)(Rc$_c$) or —N($R_{bb}$)S(O)$_2R_{bb}$). Wherein each $R_{aa}$, $R_{bb}$ and $R_{cC}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

The term "alkyl," as used herein, refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "aminoalkyl" as used herein, refers to an amino substituted C\-Cn alkyl radical. The alkyl portion of the radical forms a covalent bond with a parent molecule. The amino group can be located at any position and the aminoalkyl group can be substituted with a further substituent group at the alkyl and/or amino portions.

The terms "aralkyl" and "arylalkyl," as used herein, refer to an aromatic group that is covalently linked to a C\-Cn alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substituent groups on one or both of the heteroaryl or alkyl portions.

The following terms are defined as follows:
allyl —$CH_2CH=CH_2$,
propargyl —$CH_2C\equiv CH$,
homoallyl —$CH_2CH_2CH=CH_2$, and
homopropargyl —$CH_2CH_2C\equiv CH$.

As noted above, preferred cyclic purine dinucleotides also include prodrug forms of CDNs, and in particular CDN thiophosphates. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011.

The term "substantially pure" as used herein with regard to cyclic purine dinucleotides refers to an Rp,Rp or Rp,Sp form which is at least 75% pure relative to other possible stereochemistries at the chiral centers indicated in the figure above. By way of example, a "substantially pure Rp,Rp c-di-GMP thiophosphate" would be at least 75% pure with regard to the Rp,Sp and Sp,Sp forms of c-di-GMP thiophosphate. In preferred embodiments, a substantially pure cyclic purine dinucleotide is at least 85% pure, at least 90% pure, at least 95% pure, at least 97% pure, and at least 99% pure. While a substantially pure cyclic purine dinucleotide preparation of the invention is "stereochemically pure," this is not meant to indicate that all CDNs within the preparation having a particular stereochemistry at these chiral centers are otherwise identical. For example, a substantially pure cyclic purine dinucleotide preparation may contain a combination of Rp,Rp c-di-GMP thiophosphate and Rp,Rp c-di-AMP thiophosphate and still be a substantially pure cyclic purine dinucleotide preparation. Such a preparation may also include other components as described hereinafter that are advantageous for patient treatment, provided that all CDNs within the preparation having a particular stereochemistry at these chiral centers.

The CDN compositions described herein can be administered to a host, either alone or in combination with a pharmaceutically acceptable excipient, in an amount sufficient to modify an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the CDN compositions are administered in conjunction with one or more additional compositions. The CDN compositions may be administered before, after, and/or together with an additional therapeutic or prophylactic composition. Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). In certain embodiments the one or more therapeutics is selected from anti-TNF agents (e.g., etanercept, infliximab), steroids, azathioprine, cyclosporine, methotrexate, abatacept, PDE4 inhibitors (e.g., roflumilast), etc.

Delivery Agents

Liposomes are vesicles formed from one ("unilamellar") or more ("multilamellar") layers of phospholipid. Because of the amphipathic character of the phospholipid building blocks, liposomes typically comprise a hydrophilic layer presenting a hydrophilic external face and enclosing a hydrophilic core. The versatility of liposomes in the incorporation of hydrophilic/hydrophobic components, their non-toxic nature, biodegradability, biocompatibility, adjuvanticity, induction of cellular immunity, property of sustained release and prompt uptake by macrophages, makes them attractive candidates for the delivery of antigens.

WO2010/104833, which is incorporated by reference herein in its entirety, describes liposomal preparations which comprise:

a) an aqueous vehicle;
b) liposomes comprising
 (i) dimyristoylphosphatidylcholine ("DMPC"),
 (ii) dimyristoylphosphatidylglycerol ("DMPG"), dimyristoyltrimethylammonium propane ("DMTAP"), or both DMPG and DMTAP,
and
 (iii) at least one sterol derivative; and
c) one or more immunogenic polypeptide(s) or carbohydrate(s) covalently linked to between 1% and 100% of said at least one sterol derivative.

Such liposomal formulations, referred to herein as VesiVax® (Molecular Express, Inc.), with our without the "immunogenic polypeptide(s) or carbohydrate(s)" referred to above, can contain one or more additional components such as peptidoglycan, lipopeptide, lipopolysaccharide, monophosphoryl lipid A, lipoteichoic acid, resiquimod, imiquimod, flagellin, oligonucleotides containing unmethylated CpG motifs, beta-galactosylceramide, muramyl dipeptide, all-trans retinoic acid, double-stranded viral RNA, heat shock proteins, dioctadecyldimethylammonium bromide, cationic surfactants, toll-like receptor agonists, dimyristoyltrimethylammoniumpropane, and nod-like receptor agonists. Advantageously, these liposomal formulations can be used to deliver one or more cyclic purine dinucleotides in accordance with the present invention.

Moreover, while the liposomal formulations discussed above employ a "steroid derivative" as an anchor for attaching an immunogenic polypeptide or carbohydrate to a liposome, the steroid may simply be provided as an unconjugated steroid such as cholesterol.

Suitable methods for preparing liposomes from lipid mixtures are well known in the art. See, e.g., Basu & Basu, *Liposome Methods and Protocols* (*Methods in Molecular Biology*), Humana Press, 2002; Gregoriadis, *Liposome Technology*, 3$^{rd}$ Edition, Informa HealthCare, 2006. Preferred methods include extrusion, homogenization, and sonication methods described therein. An exemplary method for preparing liposomes for use in the present invention, which comprises drying a lipid mixture, followed by hydration in an aqueous vehicle and sonication to form liposomes, is described in WO2010/104833.

In certain embodiments, the liposomes are provided within a particular average size range. Liposome size can be selected, for example, by extrusion of an aqueous vehicle comprising liposomes through membranes having a preselected pore size and collecting the material flowing through the membrane. In preferred embodiments, the liposomes are selected to be substantially between 50 and 500 nm in diameter, more preferably substantially between 50 and 200 nm in diameter, and most preferably substantially between 50 and 150 nm in diameter. The term "substantially" as used herein in this context means that at least 75%, more preferably 80%, and most preferably at least 90% of the liposomes are within the designated range.

Other lipid and lipid-like adjuvants which may find use in the present invention include oil-in-water (o/w) emulsions (see, e.g., Muderhwa et al., J. Pharmaceut. Sci. 88: 1332-9, 1999)), VesiVax® TLR (Molecular Express, Inc.), digitonin (see, e.g., U.S. Pat. No. 5,698,432), and glucopyranosyl lipids (see, e.g., United States Patent Application 20100310602).

Nanoparticles also represent drug delivery systems suitable for most administration routes. Over the years, a variety of natural and synthetic polymers have been explored for the preparation of nanoparticles, of which Poly(lactic acid) (PLA), Poly(glycolic acid) (PGA), and their copolymers (PLGA) have been extensively investigated because of their biocompatibility and biodegradability. Nanoparticles and other nanocarriers act as potential carries for several classes of drugs such as anticancer agents, antihypertensive agents, immunomodulators, and hormones; and macromolecules such as nucleic acids, proteins, peptides, and antibodies. See, e.g., Crit. Rev. Ther. Drug Carrier Syst. 21:387-422, 2004; Nanomedicine: Nanotechnology, Biology and Medicine 1:22-30, 2005.

Pharmaceutical Compositions

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in Remington, The Science and Practice of Pharmacy 21$^{st}$ Edition (Mack Publishing Co., Easton, Pa.) and Nielloud and Marti-Mestres, Pharmaceutical Emulsions and Suspensions: 2$^{nd}$ Edition (Marcel Dekker, Inc, New York).

For the purposes of this disclosure, the pharmaceutical compositions may be administered by a variety of means including orally, parenterally, by inhalation spray, topically, or rectally in formulations containing pharmaceutically acceptable carriers, adjuvants and vehicles. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made in a suitable machine using a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

As used herein, pharmaceutically acceptable salts include, but are not limited to: acetate, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl)aminomethane. Additional pharmaceutically acceptable salts are known to those skilled in the art.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of pharmaceutical composition. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

As noted, the compositions of the present invention are preferably formulated as pharmaceutical compositions for parenteral or enteral delivery. A typical pharmaceutical composition for administration to an animal comprises a pharmaceutically acceptable vehicle such as aqueous solutions, non-toxic excipients, including salts, preservatives, buffers and the like. See, e.g., *Remington's Pharmaceutical Sciences*, 15th Ed., Easton ed., Mack Publishing Co., pp 1405-1412 and 1461-1487 (1975); *The National Formulary*

XIV, 14th Ed., American Pharmaceutical Association, Washington, D.C. (1975). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antioxidants, chelating agents and inert gases. The pH and exact concentration of the various components the pharmaceutical composition are adjusted according to routine skills in the art.

EXAMPLES

The following examples serve to illustrate the present invention. These examples are in no way intended to limit the scope of the invention.

Example 1

General Methods

Anhydrous solvents and reagents suitable for solution phase oligonucleotide synthesis were purchased and handled under dry argon or nitrogen using anhydrous technique. Amidite coupling reactions and cyclizations were carried out in anhydrous acetonitrile or pyridine under dry argon or nitrogen. The starting materials for all reactions in dry pyridine were dried by concentration (three times) from pyridine. Preparative silica gel flash chromatography was carried out using Fluka 60A high-purity grade or Merck Grade 9385 silica using gradients of methanol in dichloromethane. Analytical HPLC was carried out on a Varian ProStar 210 HPLC system with a ProStar 330 photodiode array detector monitoring at 254 nm using a either a Varian Microsorb 10 micron C18 250×4.6 mm or a Varian 3micronC18 100×4.6 mm column and gradients of 10 mM TEAA and acetonitrile. Preparative HPLC was carried out on a Shimadzu preparative LC20-AP HPLC system, equipped with a SPD-20A UV/Vis detector monitoring at 254 nm on a Varian Microsorb 60-8 C-18 41.6×250 mm column using gradients of 10 mM TEAA and acetonitrile at a flow rate of 50 ml/min Solid phase extractions using C-18 Sep-Pak (Waters) were carried out at loadings of 3% (wt/wt). LC/MS (ESI/APCI) was obtained on a single quadrapole Shimadzu 2010EV instrument with PDA, MS, and ELSD detection using a Shimadzu LC20D analytical HPLC. High resolution FT-ICR mass spec was obtained from both WM Keck Foundation Biotechnology Resource Laboratory at Yale University in New Haven, Conn., and the QB3/Chemistry Mass Spect Lab at UC Berkeley.

$^1$H, $^{31}$P, $^1$H-$^1$H COSY (2D NMR correlation spectroscopy), $^1$H-$^{31}$P HMBC (heteronuclear multiple-bond correlation spectroscopy) spectra were acquired in d6-DMSO with 10 uL D$_2$O (16 hr delay after D$_2$O addition) at 45° C. on a Varian INOVA-500 NMR spectrometer operating at 500 MHz for 1H and 202 MHz for 31P. The resulting FIDs were transferred to a PC and processed using NUTS NMR processing software from Acorn NMR Inc. The chemical shifts were referenced to the DMSO solvent, 2.50 ppm for 1H. Per IUPAC recommendations for referencing of NMR spectral, the 31P chemical shifts were referenced using the "unified scale" to the absolute 1H frequency of 0 ppm. Some of the 1H and 31P spectra were acquired on a JEOL ECX-400 NMR spectrometer operating at 400 MHz for 1H and 162 MHz for 31P. The gradient COSY spectra were acquired at 45.0° C. on a Varian INOVA-500 NMR spectrometer operating at 500 MHz for 1H and 202 MHz for 31P. The resulting FIDs were transferred to a PC and processed using NUTS NMR processing software from Acorn NMR Inc. The chemical shifts were referenced to the DMSO solvent, 2.50 ppm for 1H. Per IUPAC recommendations for referencing of NMR spectral, the 31P chemical shifts were referenced using the "unified scale" to the absolute 1H frequency of 0 ppm. The gradient COSY spectrum was acquired in absolute value mode using 2048 data points in the direct dimension and 256 time points in the indirect dimension. Both dimensions were apodized using sinebell squared functions. The indirect dimension was zero filled to give a final matrix size of 2048×2048 points and a resolution of 3.91 Hz/data point in both dimensions.

Figure 3A:
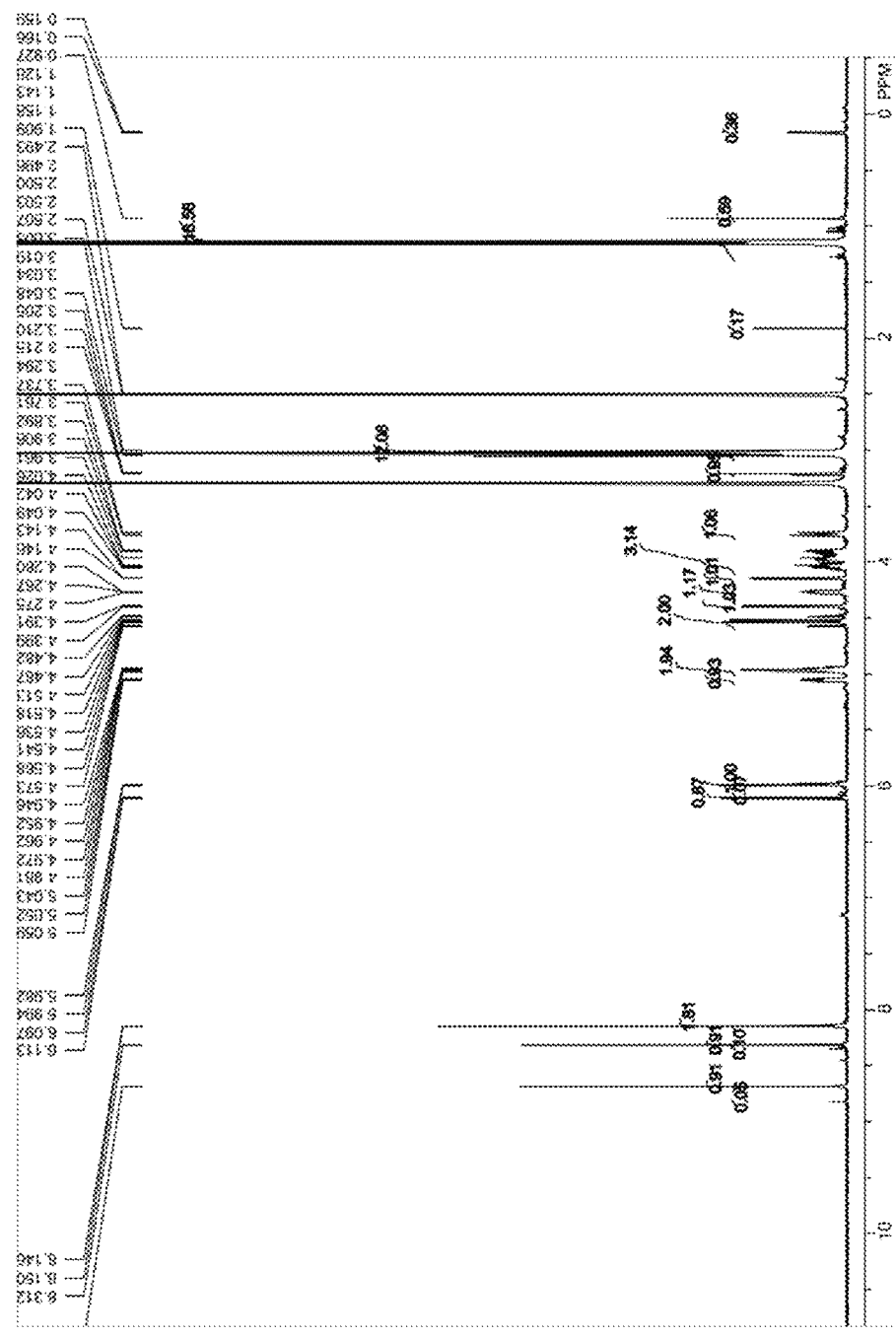
FIG. 3A depicts $^1$H NMR analytical results for 2'-O-propargyl-ML-CDA (compound 8).
Figure 3B:
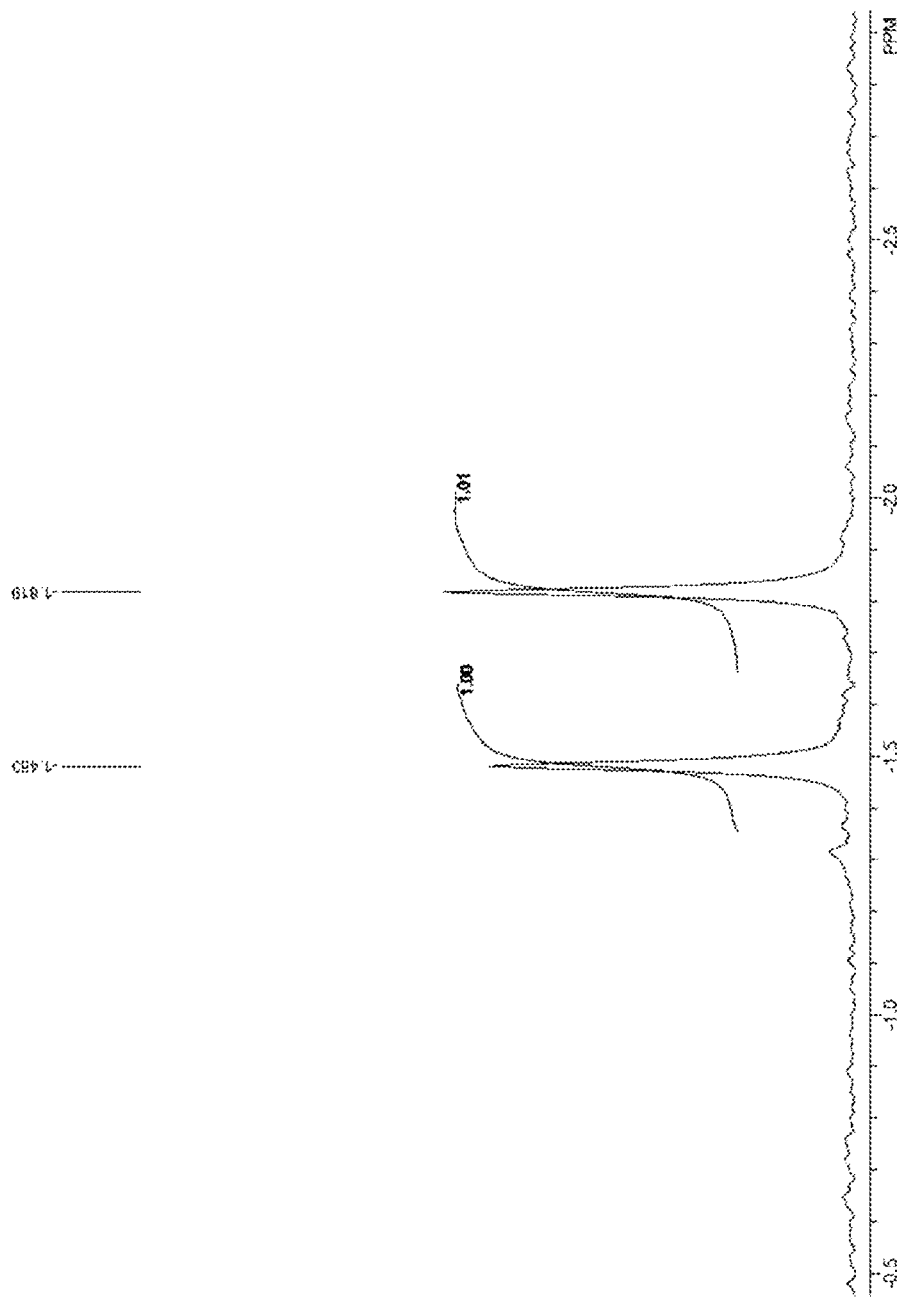
FIG. 3B depicts $^{31}$P NMR analytical results for 2'-O-propargyl-ML-CDA (compound 8).
Figure 3C:
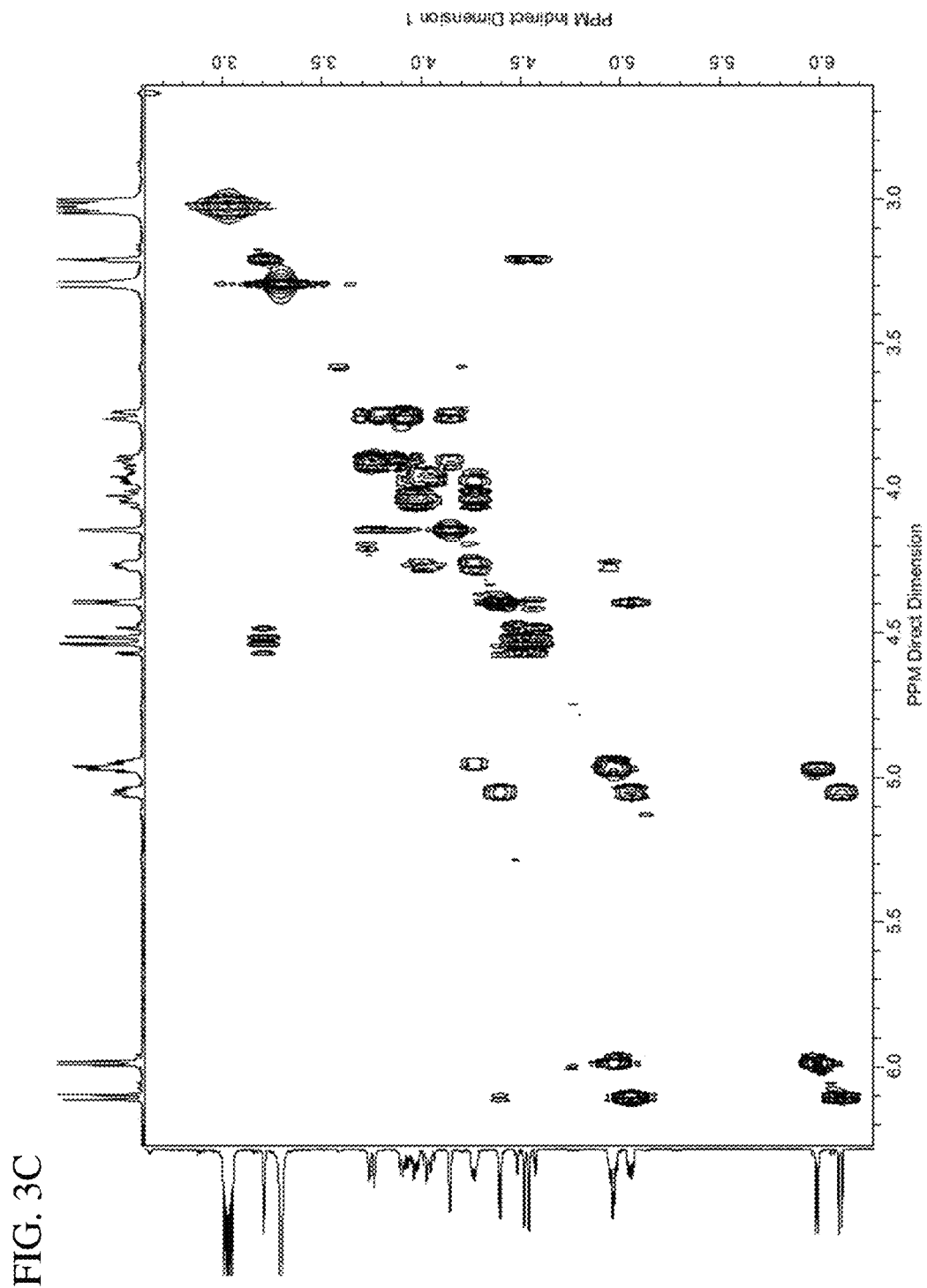
FIG. 3C depicts COSY (2.5-6.5 ppm—$^1$H axis) analytical results for 2'-O-propargyl-ML-CDA (compound 8).
Figure 3D:
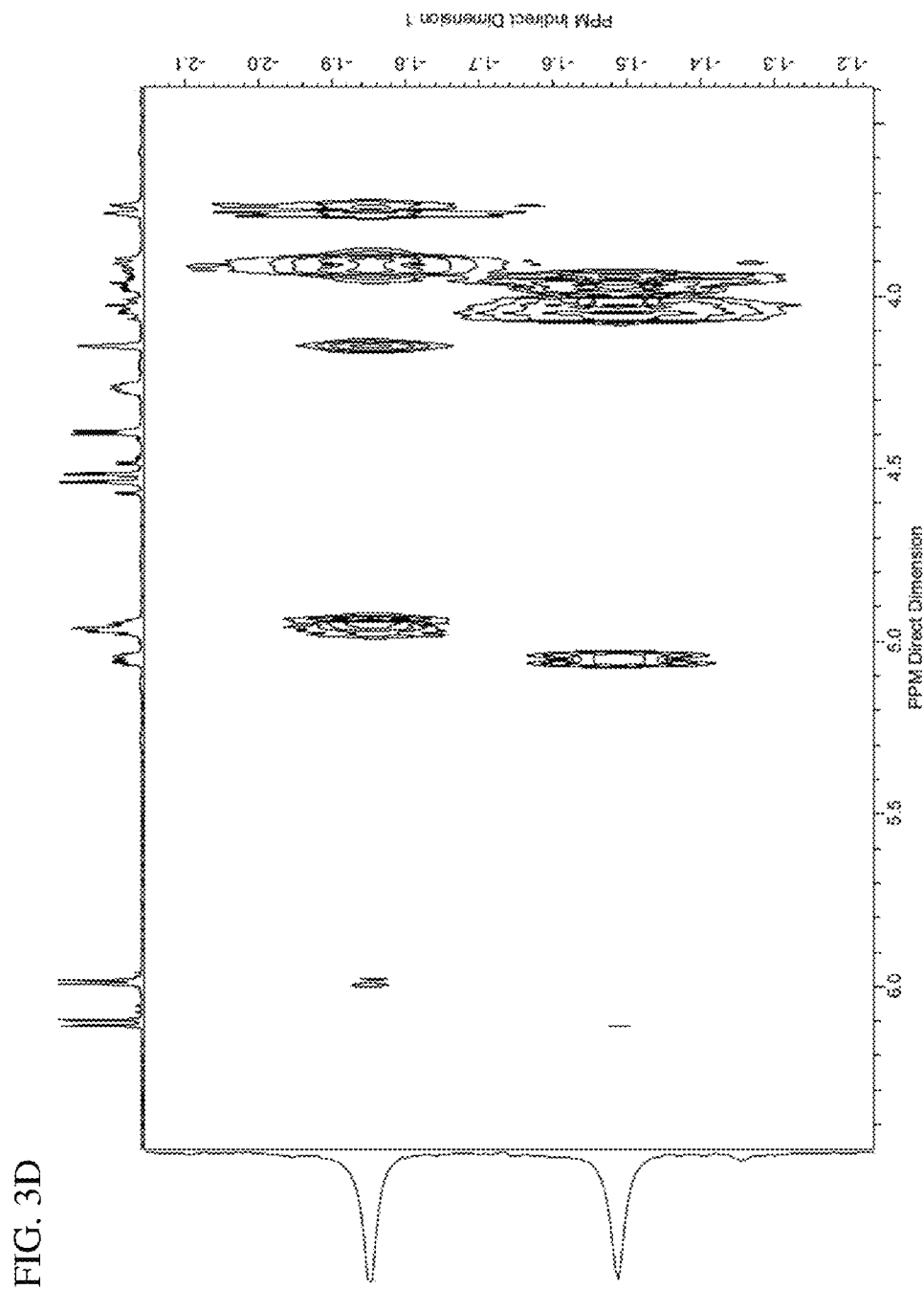
FIG. 3D depicts HMBC (3.5-6.5 ppm—$^1$H axis) analytical results for 2'-O-propargyl-ML-CDA (compound 8).
Figure 3E:
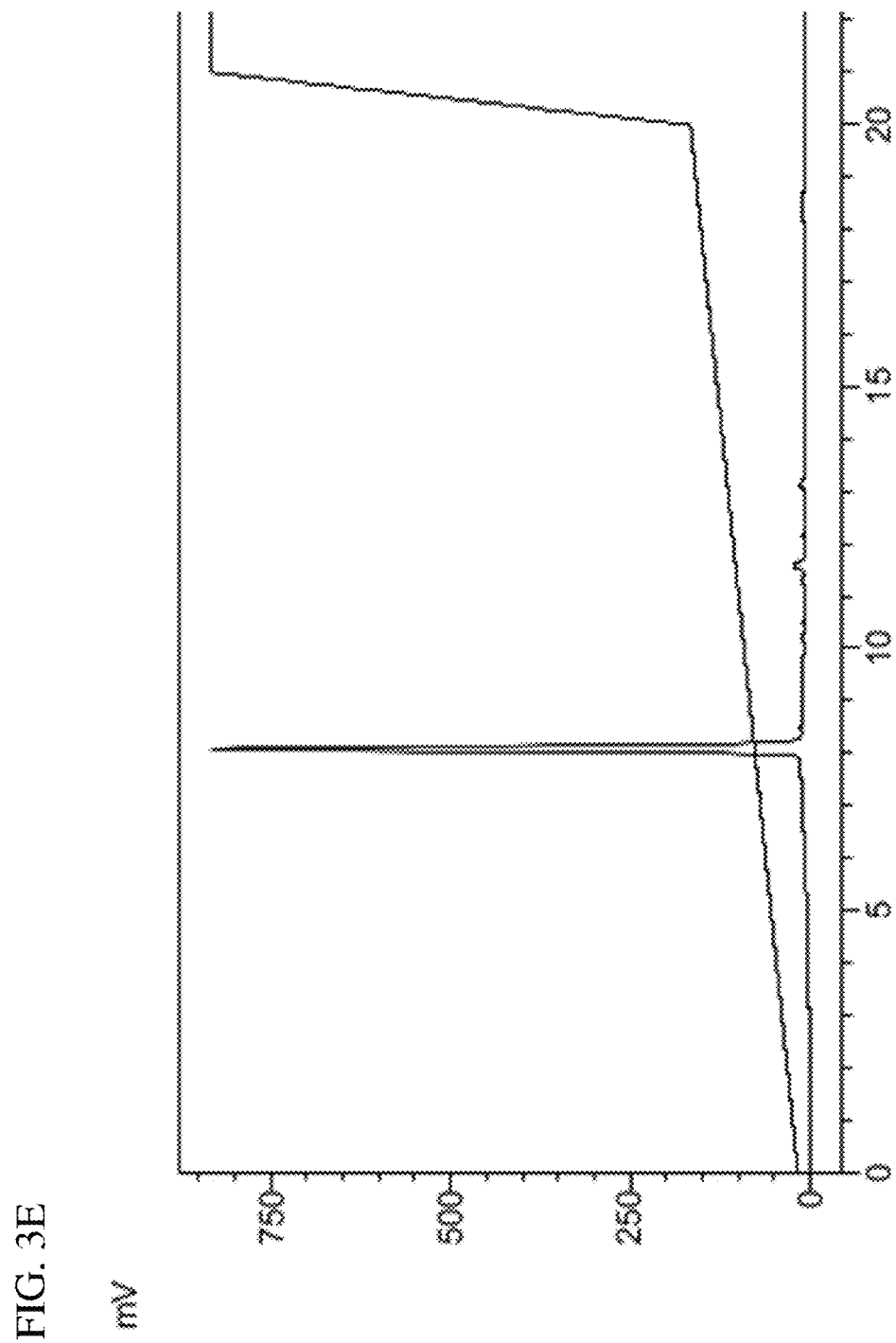
FIG. 3E depicts analytical HPLC (2-20% ACN/10 mM TEAA buffer—20 min) analytical results for 2'-O-propargyl-ML-CDA (compound 8).

Assignment of regiochemistry at phosphodiester linkage: 1H-1H COSY in combination with $^1$H-$^{31}$P HMBC experiments were used to provide direct evidence that the regiochemistry of the phosphodiester linkages are 2', 5'-3', 5' (see for example FIGS. 3C and 3D).

Abbreviations and Acronyms. Guanine=G. isobutyryl guanine=G$^{ib}$. 4,4-dimethoxytrityl=DMT. OCH$_2$CH$_2$CH$_3$=CEO. tert-butyldimethylsilyl=TBS. adenine=A. benzoyl adenine=A$^{Bz}$, 2'-O-myristoyl-cyclic-[G(2',5')pG(3',5')p]=C14-ML-CDG=10 (TEA salt). All CDN products were ≥95% pure as indicated by C18 reverse phase HPLC analysis using UV detection at 254 nm (see FIG. 2E for purity of structure 8).

Example 2

Figure 2:
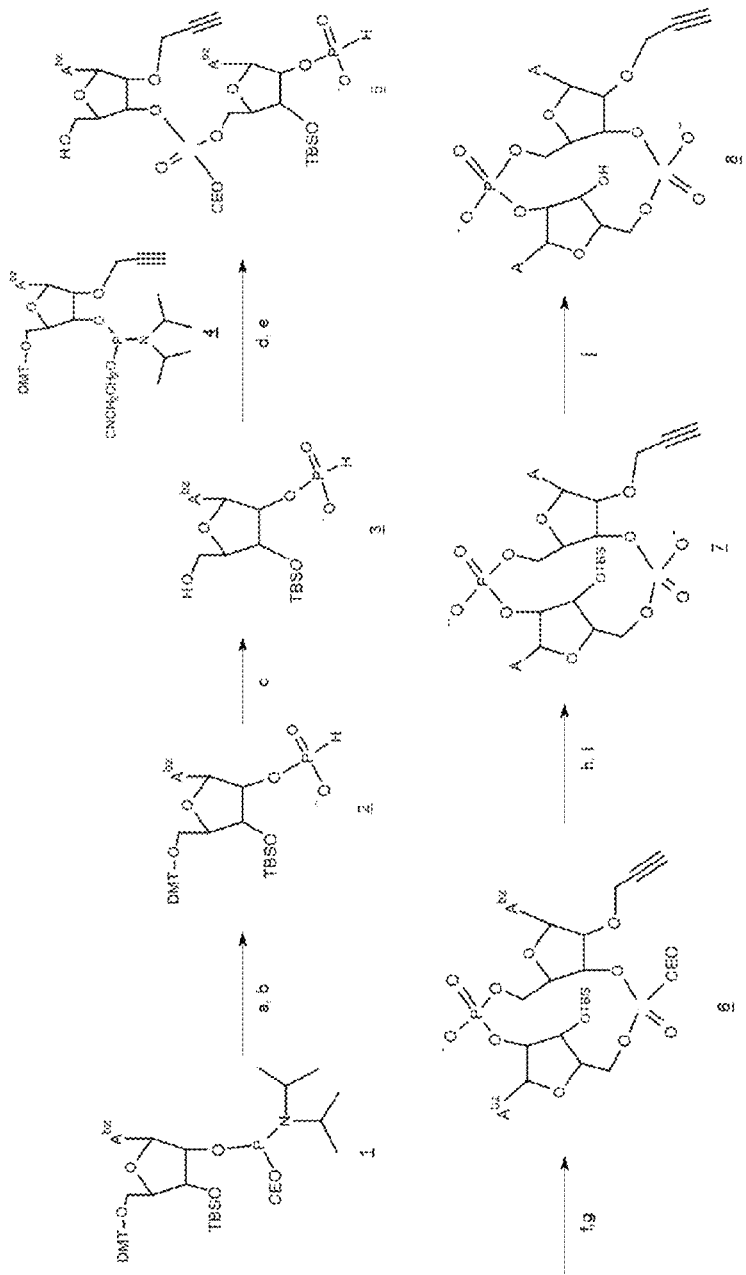
FIG. 2 depicts a synthesis scheme Synthesis of 2'-O-propargyl-cyclic-A(2',5')pA(3',5')p (2'-O-propargyl-ML-CDA).

Synthesis of 2'-O-propargyl-cyclic-A(2',5')pA(3',5')p (2'-O-propargyl-ML-CDA, structure 8), FIG. 2)

1) Preparation of 3.

To a solution of 1.7 g (1.72 mmol) N$^6$-benzoyl-5'-O-(4,4'-dimethoxytrityl)-3'-O-tert-butyldimethylsilyl-2'-O-[(2-cyanoethyl)-N,N-diisopropylaminophinyl]adenosine (1) in 7.5 ml acetonitrile was added 0.054 ml (3 mmole) water and 0.35 g (1.8 mmole) pyridinium trifluoroacetate. After 5 minutes stirring at room temperature 7.5 ml tert-butylamine was added and the reaction stirred for 15 minutes at room temperature. The solvents were removed under reduced pressure to give 2 as a foam which was then co-evaporated with acetonitrile (3×15 ml), then dissolved in 18 ml dichloromethane. To this solution was added water (0.27 ml, 15 mmole) and 18 ml of 6% (v/v) dichloroacetic acid (13.2 mmole) in dichloromethane. After 10 minutes at room temperature the reaction was quenched by the addition of pyridine (2.1 ml, 26 mmole), and concentrated to an oil which was dried by three co-evaporations with 12 ml anhydrous acetonitrile, the last time leaving 3 in a volume of ~4 ml.

2) Preparation of a Dry Solution of 4.

N$^6$-benzoyl-5'-O-(4,4'-dimethoxytrityl)-2'-O-propargyl-3'-O-[(2-cyanoethyl)-N,N-diisopropylaminophinyl]adenosine (4, 2 g, 2.2 mmole) was dissolved in 25 ml anhydrous acetonitrile and dried by three co-evaporations with 25 ml anhydrous acetonitrile, the last time leaving ~6 ml. Ten 3 Å molecular sieves were added and the dried solution stored under argon until use.

3) Preparation of 2',5'-Linear Dimer 5.

Azeo dried 4 (2 g, 2.2 mmole) in ~6 ml acetonitrile was added via syringe to a solution of 3 (1.72 mmole) in ~4 ml of anhydrous acetonitrile. After 5 minutes stirring at room temperature, 0.82 ml (4.5 mmole) of 5.5M tert-butyl hydroperoxide in decane was added and the reaction stirred for 30 minutes at room temperature. The reaction was cooled in an ice bath, and 0.38 g NaHSO₃ in 0.75 ml water was added and stirred at room temperature for 5 minutes. The reaction was concentrated and the residual oil dissolved in 24 ml dichloromethane. Water (0.27 ml, 15 mmole) and 24 ml of 6% (v/v) dichloroacetic acid (17.4 mmole) in dichloromethane was added, and the reaction stirred for 10 minutes at room temperature. 15 ml pyridine was added to quench the dichloroacetic acid, which was then concentrated down to ~4 ml.

4) Cyclization and Oxidation of 5 to Give the Fully-Protected-Propargyl-Cyclic-Dinucleotide 6.

5 was dissolved in 45 ml dry pyridine which was concentrated down to a volume of approximately 30 ml. 2-chloro-5,5-dimethyl-1,3,2-dioxaphosphorinane-2-oxide (DMOCP, 1 g, 5.2 mmole) was then added and the reaction stirred for 10 minutes at room temperature. 1 ml water was added immediately followed by addition of I₂ (0.5 g, 2 mmole), and the reaction stirred for 5 minutes at room temperature. The reaction mix was then poured into 210 ml water containing 0.3 g NaHSO₃ and stirred for 5 minutes at room temperature. 6 g NaHCO₃ was slowly added and stirred for 5 minutes at room temperature, then poured into a separatory funnel and extracted with 250 ml 1:1 ethyl acetate:diethyl ether. The aqueous layer was extracted again with 60 ml 1:1 ethyl acetate:diethyl ether. The organic layers were combined and concentrated under reduced pressure to yield approximately 5.6 g of an oil containing fully-protected-propargyl cyclic dinucleotide 6.

6) Deprotection of the Fully-Protected-Propargyl Cyclic Dinucleotide 6 to Crude 7.

5.6 g of crude 6 was transferred to a thick-walled glass pressure tube. 30 ml methanol and 30 ml concentrated aqueous ammonia was added and the tube was heated with stirring in an oil bath at 55° C. for 4 h, at which time analytical HPLC showed deprotection was complete. The reaction mixture was cooled to near ambient temperature, sparged with a stream of argon gas for 30 minutes, and then transferred to a large round bottom flask. Most of the volatiles were removed under reduced pressure to give a residue of 4.7 g, which was triturated against 20 ml 1:1 (v/v) dichloromethane:hexane. Any remaining solvent was removed under reduced pressure to give 4.5 g of a solid containing 7.

7) Preparative HPLC Purification of Crude 7 to Give Pure 7.

The crude solid containing 7 was taken up in 25 ml of CH₃CN/water (1:1). After 0.45 micron PTFE filtration, 4-5 ml sample portions were applied to a C-18 Dynamax column (40×250 mm) Elution was performed with a gradient of acetonitrile and 10 mM aqueous triethylammonium acetate (20% to 50% CH₃CN over 20 minutes at 50 ml/min flow). Fractions from the preparative HPLC runs containing pure 7 were pooled, evaporated to remove most of the CH₃CN and water and coevaporated several times with CH₃CN to give 55 mg of pure 7.

8) Deprotection of the TBS Group of 7 with Triethylamine Trihydrofluoride, Neutralization with TEAB, Solid Phase Extraction with a C-18 Sep-Pak and Lyophilization to Give Pure 8 as the Bis-Triethylammonium Salt.

To 55 mg of 7 was added 1.0 ml of neat triethylamine trihydrofluoride. The mixture was stirred at room temperature for approximately 3 h. The mixture was then transferred to an oil bath at 50° C. for an additional 2 hours, at which time analytical HPLC confirmed completion of the reaction. The sample was neutralized by dropwise addition into 5 ml of chilled, stirred 1M triethylammonium bicarbonate. Approximately 1-2 ml TEA was added dropwise to the stirred, chilled solution until pH paper showed neutral/slightly basic (~pH8) conditions were achieved. The neutralized solution was desalted on a Waters C-18 Sep-Pak and the product eluted with CH₃CN/10 mM aqueous triethylammonium acetate (15:85). The CH₃CN was evaporated under reduced pressure and the solution was frozen and lyophilized. An additional round of lyophilization from water gave 9 mg (13 μmole) of 2'-O-propargyl-ML-CDA (8) as the bis-triethylammonium salt. $^1$H NMR (500 MHz, 45° C., DMSO-D₆+15 μL D₂O) δ 8.68 (s, 1H), 8.31 (s, 1H), 8.15 (s, 1H), 8.14 (s, 1H), 6.10 (d, J=8.0, 1H), 5.99 (d, J=6.0, 1H), 5.06-5.04 (m, 1H), 4.98-4.94 (m, 1H), 4.53 (qt, J=16.0, 2.5, 2H), 4.39 (d, J=4.0, 1H), 4.27-4.26 (m, 1H), 4.14-4.13 (m, 1H), 4.05-3.90 (m, 3H), 3.74 (d, J=12.0, 1H), 3.21 (t, J=2.5, 1H), 3.03 (q, J=7.0, 12H), 1.14 (t, J=7.5, 19H); $^{31}$P NMR (200 MHz, 45° C., DMSO-D₆+15 μL D₂O) δ −1.48, −1.82 (FIG. 3A-3D); HRMS (FT-ICR) m/z: [M-H]⁻ calcd for $C_{23}H_{25}N_{10}O_{12}P_2$ 695.1134. found 695.1118.

Figure 4:
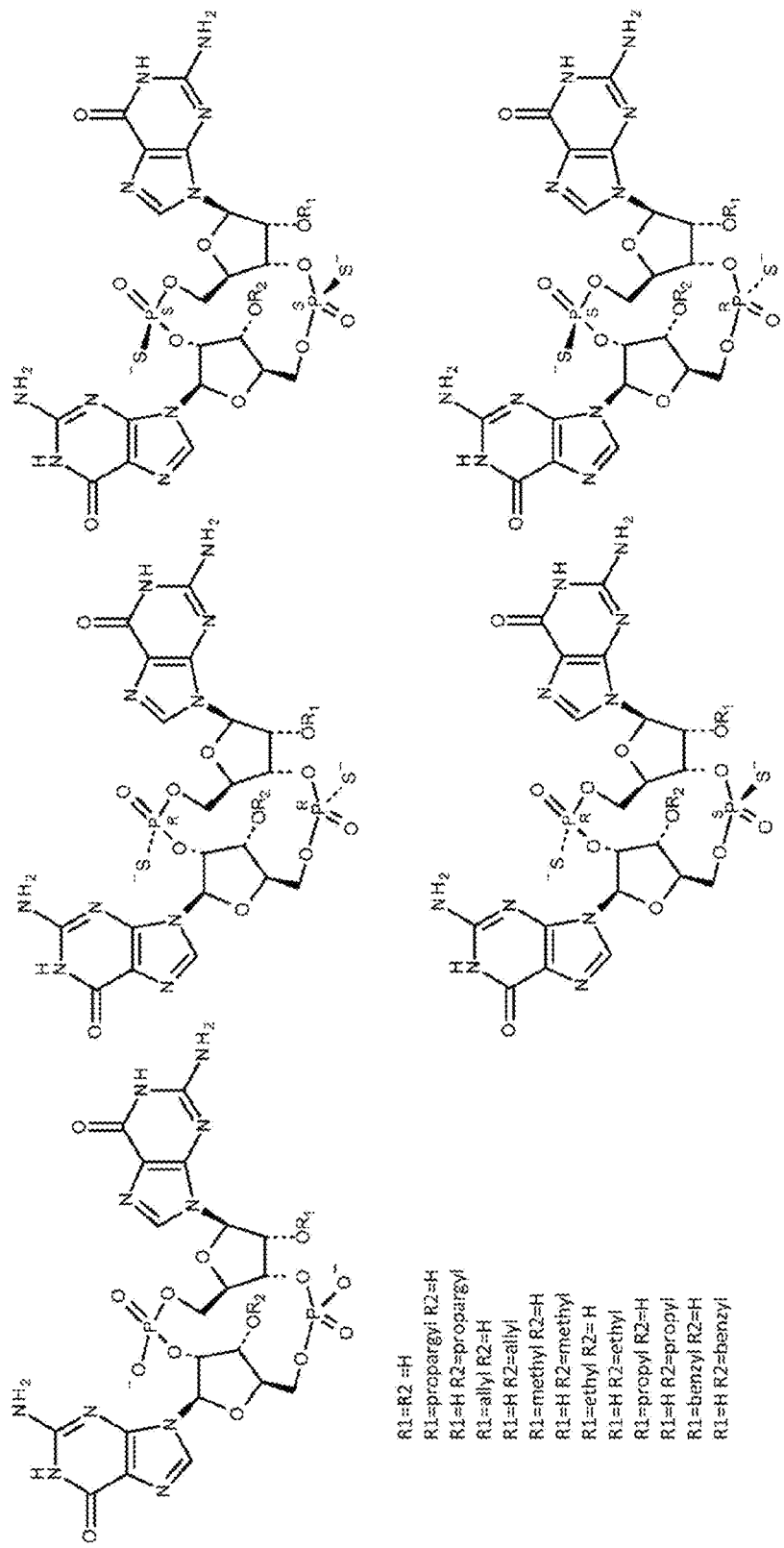
FIG. 4 depicts c-[G(2',5')pG(3',5')p] and dithio ribose O-substituted derivatives.
Figure 5:
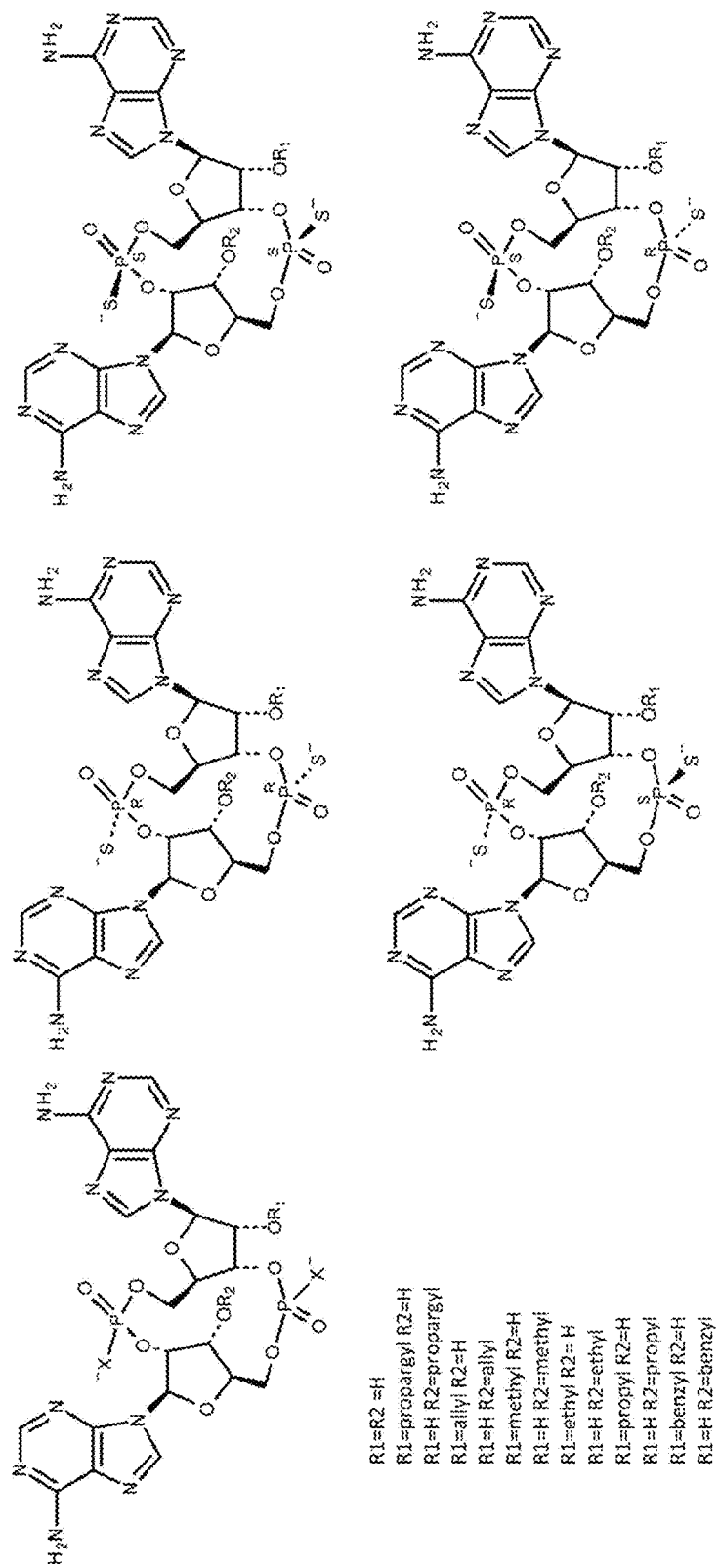
FIG. 5 depicts c-[A(2',5')pA(3',5')p] and dithio ribose O-substituted derivatives.
Figure 6:
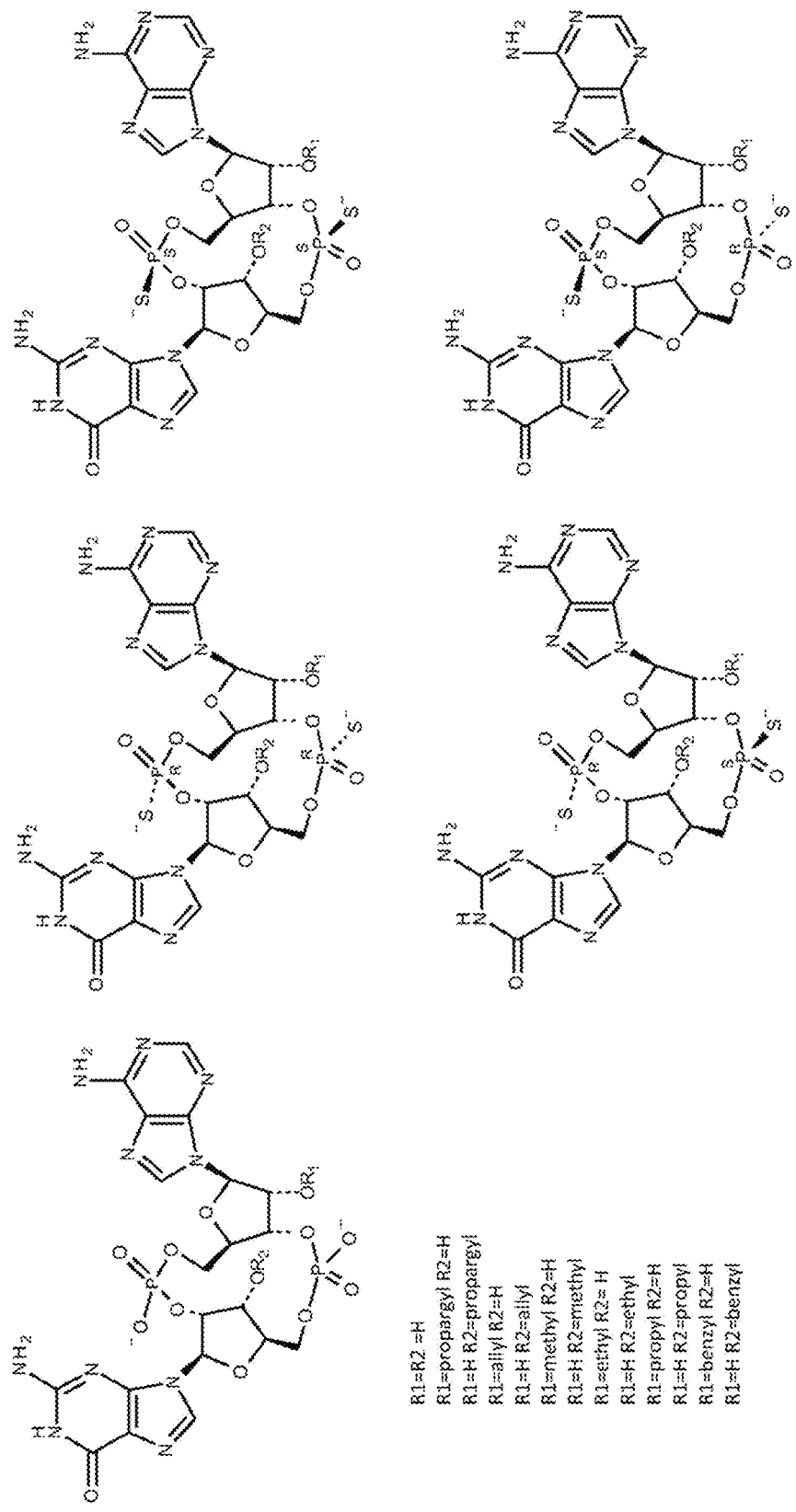
FIG. 6 depicts c-[G(2',5')pA(3',5')p] and dithio ribose O-substituted derivatives.

FIGS. 4-6 depict alternative compounds which may be made by analogous methods to those described herein.

Example 3

Inhibition of STING-Dependent Responses

To evaluate if the antagonist 2'-O-propargyl-cyclic-[A(2',5')pA(3',5')p] (ML-propargyl-CDA) can inhibit STING-dependent induction of type I interferon induction by Rp, Rp dithio cyclic [A(2',5')pA(3',5')p] (ML RR-CDA) in human cells, 4×10⁵ THP1-Blue™ ISG cells (a human monocyte cell line transfected with an IRF-inducible secreted embryonic alkaline phosphatase reporter gene (Invivogen) which express alkaline phosphatase under the control of a promoter comprised of five IFN-stimulated response elements) were incubated with 50 μM of Rp, Rp dithio cyclic [A(2',5')pA(3',5')p] (ML RR-CDA), 10 μM or 50 μM of the antagonist 2'-O-propargyl-cyclic-[A(2',5')pA(3',5')p] (ML-propargyl-CDA), both 50 μM Rp, Rp dithio cyclic [A(2',5')pA(3',5')p] (ML RR-CDA) and 10 μM or 50 μM 2'-O-propargyl-cyclic-[A(2',5')pA(3',5')p] (ML-propargyl-CDA), or 50 μM Rp, Rp dithio cyclic [A(2',5')pA(3',5')p] (ML RR-CDA) after a 30 min pre-incubation with 10 μM 2'-O-propargyl-cyclic-[A(2',5')pA(3',5')p] (ML-propargyl-CDA). After 30 minutes, cells were washed and plated in 96-well dish in RPMI media containing 10% FBS, and incubated at 37° C. with 5% CO₂. Cell culture supernatants from each sample were collected after 16 hr incubation, and 20 μL of the cell culture supernatants was added to 180 μL QUANTI-Blue reagent (Invivogen) and incubated for 5 minutes to evaluate type I interferon protein levels. Readings at Absorbance 655 nm were measured with a Versa Max kinetic spectrophotometer (Molecular Diagnostics).

Figure 7:
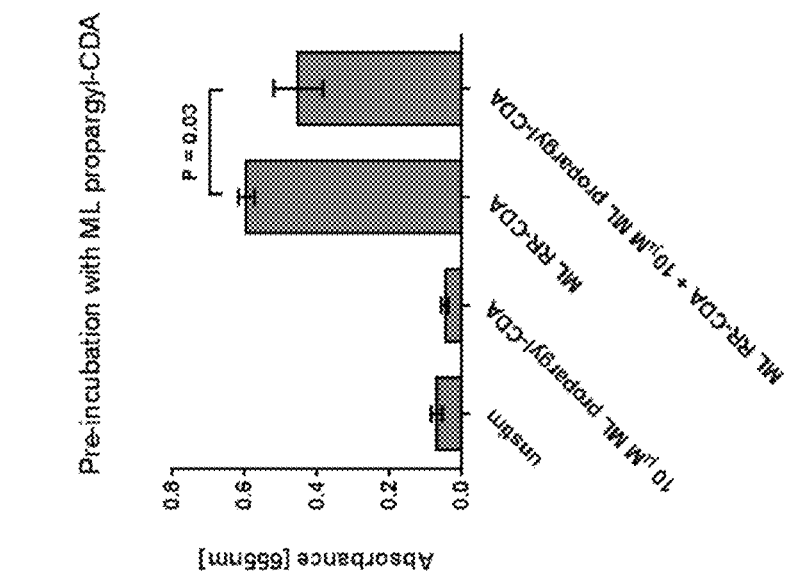
FIG. 7 depicts 2'-O-propargyl-cyclic-[A(2',5')pA(3',5')p] (2'-O-propargyl-ML-CDA) inhibition of STING-dependent activation of type I interferon.
Figure 7:
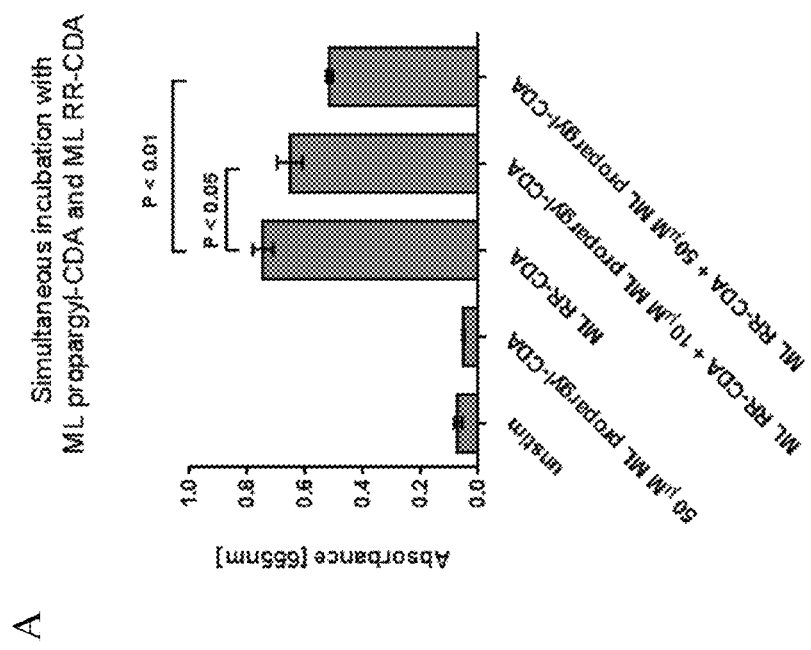

As shown in FIG. 7A, addition of 10 μM or 50 μM of the antagonist 2'-O-propargyl-cyclic-[A(2',5')pA(3',5')p] (ML-propargyl-CDA) with 50 μM Rp, Rp dithio cyclic [A(2',5')pA(3',5')p] (ML RR-CDA) significantly inhibited the induction of type I IFN by Rp, Rp dithio cyclic [A(2',5')pA(3',5')p] (ML RR-CDA) in a dose-dependent manner. FIG. 7B shows that pre-incubation with 10 μM 2'-O-propargyl-cyclic-[A(2',5')pA(3',5')p] (ML-propargyl-CDA) inhibits induction of type I interferon by the subsequent addition of 50 μM Rp, Rp dithio cyclic [A(2',5')pA(3',5')p] (ML RR-CDA). It is known that cyclic dinucleotides such as Rp, Rp dithio cyclic [A(2',5')pA(3',5')p] (ML RR-CDA) induce type I IFN signaling via STING. Therefore, the reduction in Rp, Rp dithio cyclic [A(2',5')pA(3',5')p] (ML RR-CDA)-induced type I IFN production by 2'-O-propargyl-cyclic-[A(2',5')pA (3',5')p] (ML-propargyl-CDA) demonstrates that 2'-O-propargyl-cyclic-[A(2',5')pA(3',5')p] (ML-propargyl-CDA) is an antagonist of human STING.

Structural studies of apo and cyclic di-nucleotide-bound forms of STING have shown that STING forms a symmetrical v-shaped dimer in the free and bound states with the cyclic di-nucleotide bound in a pocket formed by the dimer interface (Gao P., et al., (2013). *Cell* 154, 748-762 and reviewed in Burdette and Vance, (2013) *Nature Immunology* 14, 19-26). STING undergoes a large conformational switch upon ligand binding from a more "open" conformation in the apo form to a "closed" conformation with a four-stranded antiparallel β sheet lid forming over the ligand-binding.

The results shown here demonstrate that 2'-O-propargyl-cyclic-[A(2',5')pA(3',5')p] (ML-propargyl-CDA) can bind in the same binding pocket formed by the interface of two STING dimers. Binding of 2'-O-propargyl-cyclic-[A(2',5') pA(3',5')p] (ML-propargyl-CDA) within the pocket would prevent the binding of an activating cyclic di-nucleotide. The propargyl group on 2'-O-propargyl-cyclic-[A(2',5')pA (3',5')p] (ML-propargyl-CDA) extending from the antagonist molecule residing in the STING binding pocket sterically blocks formation of the antiparallel β sheet lid over the ligand-binding pocket, thereby preventing STING from transitioning to the signaling competent conformation. Collectively these results indicate that 2'-O-propargyl-cyclic-[A (2',5')pA(3',5')p] (ML-propargyl-CDA) is capable of inhibiting the activity of human STING.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A composition comprising a cyclic dinucleotide selected from the group consisting of:

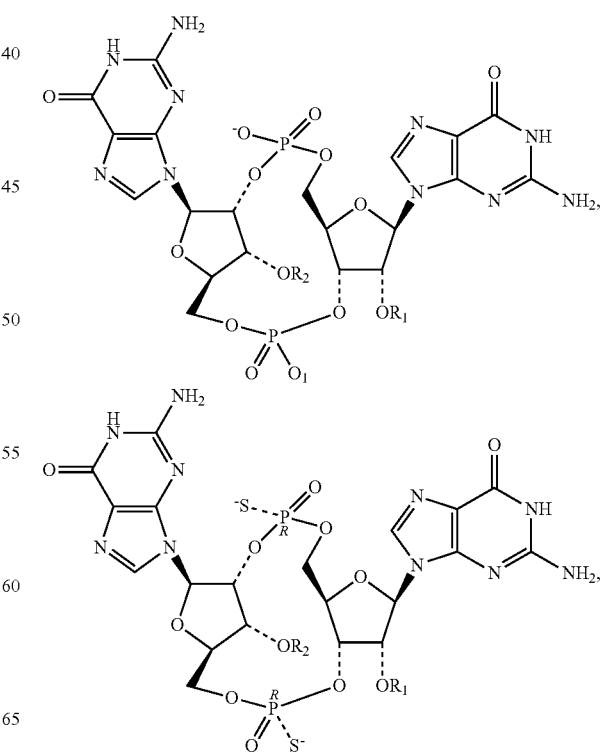

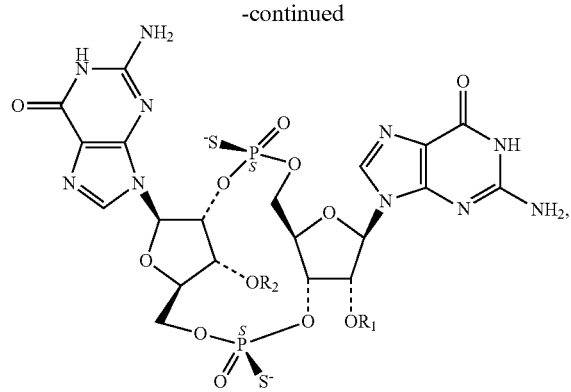
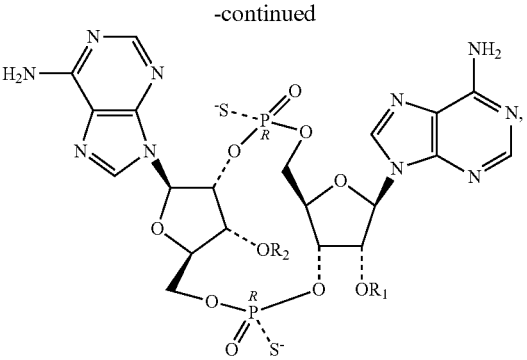

-continued

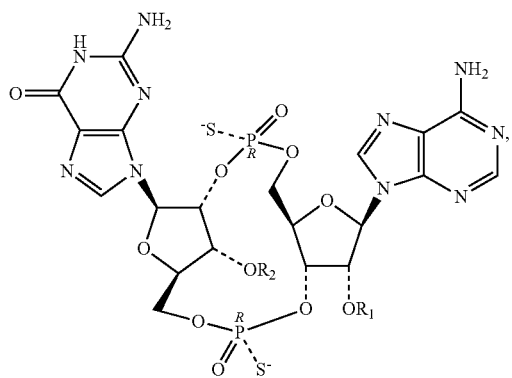

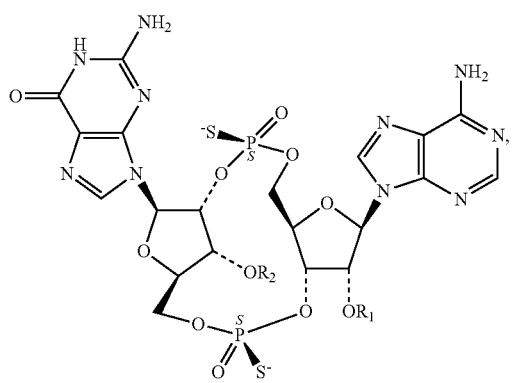

-continued

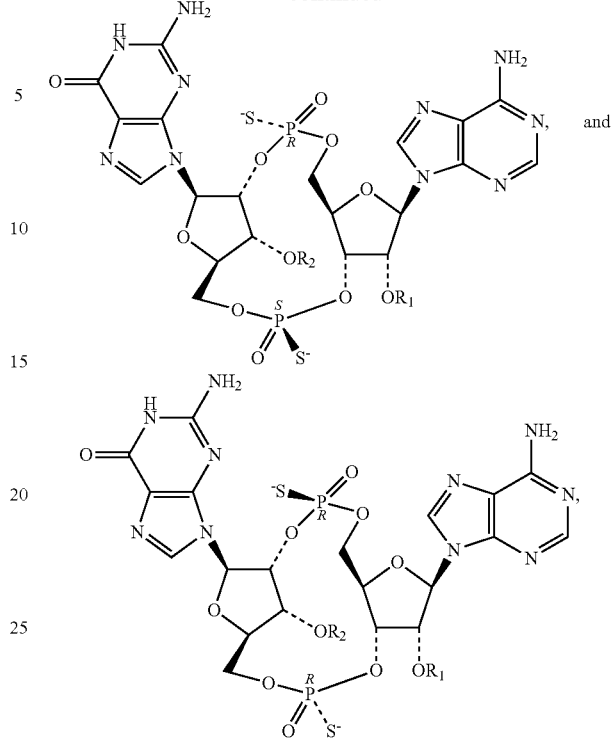

wherein $R_1$ is H and $R_2$ is propargyl, or wherein $R_1$ is propargyl and $R_2$ is H.

2. A method of inhibiting STING-dependent type I Interferon production in an individual in need thereof, comprising:
   administering a composition according to claim 1 to the individual in an amount sufficient to inhibit STING-dependent type I Interferon production.

3. A method according to claim 2, wherein the administration is parenteral.

4. A method according to claim 3, wherein the administration is subcutaneous, intramuscular, or intradermal.

* * * * *